(12) United States Patent
Southerland, III et al.

(10) Patent No.: US 11,998,324 B2
(45) Date of Patent: *Jun. 4, 2024

(54) BIOMARKER MONITORING FITNESS SYSTEM

(71) Applicant: TT1 Products, Inc., Atlanta, GA (US)

(72) Inventors: Harold Philpott Southerland, III, Atlanta, GA (US); Todd Furneaux, Atlanta, GA (US); Juan Pablo Frias, Atlanta, GA (US); Roger Steven Mazze, Excelsior, MN (US)

(73) Assignee: TT1 Products, Inc., Atlanta, GA (US)

( * ) Notice: Subject to any disclaimer, the term of this patent is extended or adjusted under 35 U.S.C. 154(b) by 238 days.

This patent is subject to a terminal disclaimer.

(21) Appl. No.: 17/509,386

(22) Filed: Oct. 25, 2021

(65) Prior Publication Data

US 2022/0039704 A1    Feb. 10, 2022

Related U.S. Application Data

(63) Continuation of application No. 17/008,577, filed on Aug. 31, 2020, now Pat. No. 11,154,223.

(Continued)

(51) Int. Cl.
*A61B 5/145* (2006.01)
*A61B 5/00* (2006.01)
*A61B 5/11* (2006.01)

(52) U.S. Cl.
CPC ........ *A61B 5/14532* (2013.01); *A61B 5/0004* (2013.01); *A61B 5/0024* (2013.01);

(Continued)

(58) Field of Classification Search
CPC ... A61B 5/0004; A61B 5/0024; A61B 5/1112; A61B 5/14532; A61B 5/6801;

(Continued)

(56) References Cited

U.S. PATENT DOCUMENTS 8,326,546 B2   12/2012   Stewart et al.
8,352,196 B2   1/2013    Vering et al.

(Continued)

FOREIGN PATENT DOCUMENTS

EP   1972270      11/2010
EP   2339953 B1   1/2018

(Continued)

OTHER PUBLICATIONS

International Search Report & Written Opinion dated Jan. 25, 2021 for International Patent Application No. PCT/US20/48851.

(Continued)

*Primary Examiner* — Eric J Messersmith
(74) *Attorney, Agent, or Firm* — Morris, Manning & Martin, LLP; Daniel E. Sineway, Esq.

(57) ABSTRACT

Disclosed herein are systems and processes for measuring, monitoring, processing, and visualizing biological data including blood glucose levels. In various embodiments, a biomarker monitoring fitness system may facilitate one or more of the monitoring of fitness data including blood glucose levels measured by continuous glucose monitoring (CGM) sensor for an individual user or group of users, the prediction of carbohydrate intake needs or insulin delivery needs during physical activity of a user and the active indication thereof to the user and/or a delivery system of the user, and the collection and management of de-identified and identifiable user fitness data including blood glucose data.

20 Claims, 13 Drawing Sheets

Related U.S. Application Data

(60) Provisional application No. 62/894,155, filed on Aug. 30, 2019.

(52) U.S. Cl.
CPC .......... *A61B 5/1112* (2013.01); *A61B 5/6801* (2013.01); *A61B 5/7292* (2013.01); *A61B 5/742* (2013.01)

(58) Field of Classification Search
CPC ... A61B 5/7292; A61B 5/742; A61B 2503/10; A61B 5/002; A61B 5/0205; A61B 5/02055; A61B 5/021; A61B 5/024; A61B 5/0816; A61B 5/1118; A61B 5/1451; A61B 5/14539; A61B 5/14542; A61B 5/14546; A61B 5/165; A61B 5/4266; A61B 5/4806; A61B 5/4875; A61B 5/6803; A61B 5/681; A61B 5/6831; A61B 5/6833; A61B 5/6867; A61B 5/7475; H01L 29/4011; H01L 29/40117; H01L 29/792; H10B 41/20; H10B 43/20; H10B 43/27; H10B 43/30
See application file for complete search history.

(56) References Cited

U.S. PATENT DOCUMENTS

| | | |
|---|---|---|
| 9,498,165 B2 | 11/2016 | Johnson et al. |
| 10,771,607 B2 | 9/2020 | Mandapaka et al. |
| 10,867,420 B2 | 12/2020 | Zamanakos et al. |
| 11,020,027 B2 | 6/2021 | Park et al. |
| 2003/0217966 A1 | 11/2003 | Tapsak et al. |
| 2006/0189863 A1 | 4/2006 | Peyser et al. |
| 2007/0083335 A1 | 4/2007 | Moerman |
| 2009/0271729 A1 | 10/2009 | Killoren et al. |
| 2010/0298685 A1 | 11/2010 | Hayter et al. |
| 2011/0245634 A1 | 10/2011 | Ray et al. |
| 2013/0096842 A1 | 8/2013 | Sato et al. |
| 2014/0005499 A1 | 1/2014 | Catt et al. |
| 2014/0088393 A1 | 3/2014 | Bernstein et al. |
| 2014/0200426 A1 | 7/2014 | Taub et al. |
| 2014/0313052 A1 | 10/2014 | Yarger et al. |
| 2017/0071511 A1 | 3/2017 | Garcia et al. |
| 2018/0235524 A1 | 8/2018 | Dunn et al. |
| 2018/0256103 A1 | 9/2018 | Cole et al. |
| 2019/0083013 A1* | 3/2019 | Park ................ A61B 5/157 |
| 2019/0320976 A1 | 10/2019 | Roslin et al. |
| 2019/0348164 A1 | 11/2019 | Bengtsson et al. |
| 2020/0164209 A1 | 5/2020 | Hogg et al. |
| 2020/0196865 A1 | 6/2020 | Kamath et al. |
| 2020/0203012 A1 | 6/2020 | Kamath et al. |
| 2020/0272319 A1 | 8/2020 | Bhavaraju et al. |

FOREIGN PATENT DOCUMENTS

| | | |
|---|---|---|
| EP | 2006786 | 5/2018 |
| WO | 2011133768 A1 | 10/2011 |
| WO | 2018125841 | 5/2018 |
| WO | 2018125841 A8 | 9/2018 |

OTHER PUBLICATIONS

Extended European Search Report for European Application No. 20200859341, dated Jun. 9, 2023, 7 Pages.

International Preliminary Report on Patentability for International Application No. PCT/US2020/048851, dated Mar. 10, 2022, 16 Pages.

* cited by examiner

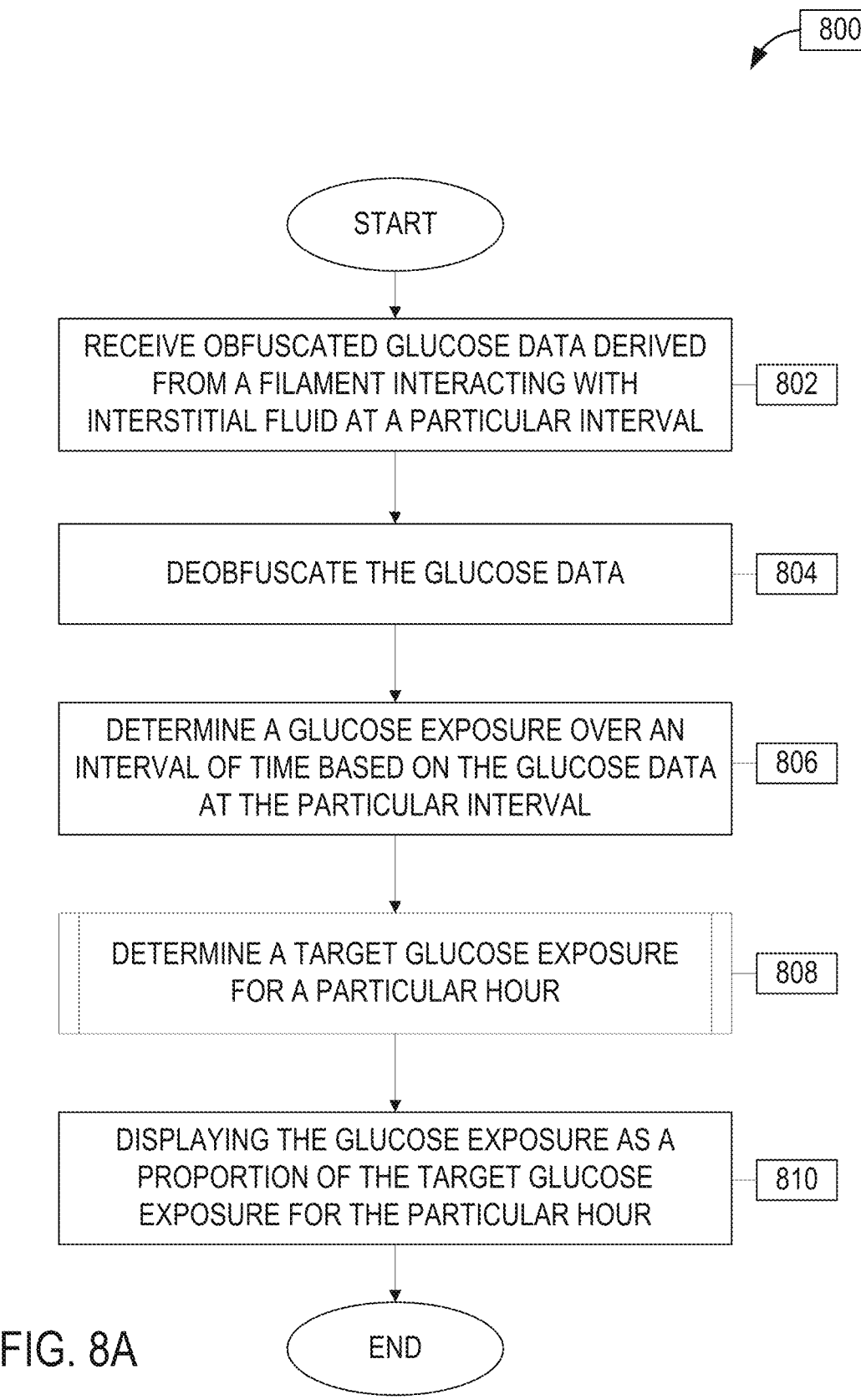

BIOMARKER MONITORING FITNESS SYSTEM

CROSS REFERENCE TO RELATED APPLICATIONS

This application is a continuation of and claims priority to U.S. patent application Ser. No. 17/008,577, filed Aug. 31, 2020, and entitled "BIOMARKER MONITORING FITNESS SYSTEM", which claims the benefit of and priority under 35 U.S.C. § 119 to U.S. Provisional Patent Appln. No. 62/894,155 filed on Aug. 30, 2019, and entitled "BIOMARKER MONITORING FITNESS SYSTEM," the disclosures of which are incorporated herein by reference in their entireties.

FIELD OF DISCLOSURE

The present disclosure relates to monitoring systems for biological data. More specifically, the present disclosure relates to systems and processes for the measurement, monitoring, processing, and visualization of information including blood glucose levels and other fitness data.

BACKGROUND

Historically, there is lack of viable data on both wide and narrow scale to inform whether, when, and how strenuously to engage in physical activity with respect to biological measures including blood glucose levels, particularly highly strenuous physical activity such as endurance sports (e.g. cycling, swimming, running), and particularly with respect to type 1 diabetes. There is also currently limited data precision for biological measures including blood glucose levels, with regard to instant and long-term impacts of physical exertion on insulin resistance, insulin delivery needs, carbohydrate intake needs, and physical activity safety/threshold indicia for people having diabetes or pre-diabetes.

Therefore, there is a long-felt but unresolved need for a continuous glucose monitoring system that in a manner and form factor suitable for engagement in physical activity, including but not limited to, carbohydrate tracking, capacity for prediction of physical activity-context blood glucose levels, insulin needs, and carbohydrate intake needs, capacity for alerting users (and/or or their delivery systems) to instant, blood glucose data-informed, carbohydrate intake or insulin delivery needs, including blood glucose data.

BRIEF OVERVIEW

Examples described herein include a biomarker monitoring fitness system that, in various embodiments, may address issues associated with carbohydrate intake needs in athletics, for example, carbohydrate intake in non-diabetic people, insulin delivery and carbohydrate intake in diabetic people, and aggregating data including lactate, ketone, and/or blood glucose data.

According to a first aspect, the biomarker monitoring fitness system may include a wearable computing device wirelessly connected to a sensor including a filament interacting with interstitial fluid and including: a display; and an integration module configured to synchronize glucose data received from the sensor and additional biomarker data; and configured for: A) deobfuscating glucose data received from the sensor on a particular interval; B) determining a glucose exposure for a particular hour based on the glucose data received on the particular interval; C) determining a target glucose exposure for the particular hour by multiplying a glucose exposure limit per hour by a numerical representation of the particular hour; D) measuring the additional biomarker data including one or more of cardiovascular, pulmonary, and perspiratory data; E) integrating the glucose exposure for the particular hour and additional biomarker data via the integration module for display; and F) displaying the glucose exposure for the particular hour as a proportion of the target glucose exposure for the particular hour and the additional biomarker data on the display.

According to a second aspect, the biomarker monitoring fitness system of the first aspect or any other aspect, wherein deobfuscating glucose data includes decrypting the glucose data.

According to a third aspect, the biomarker monitoring fitness system of the second aspect or any other aspect, wherein the glucose data includes a glucose reading taken from the filament interacting with interstitial fluid.

According to a fourth aspect, the biomarker monitoring fitness system of the first third or any other aspect, wherein the wearable computing device is configured for transmitting the glucose data and an identifier associated with the patient to a remote server.

According to a fifth aspect, the biomarker monitoring fitness system of the fourth aspect or any other aspect, wherein the glucose data includes the identifier.

According to a sixth aspect, the biomarker monitoring fitness system of the fourth aspect or any other aspect, wherein the wearable computing device associates the identifier with the received glucose data.

According to a seventh aspect, the biomarker monitoring fitness system of the third aspect or any other aspect, wherein the wearable computing device is configured for determining an average glucose level for the particular hour by averaging one or more glucose readings received on the particular interval during the particular hour.

According to an eighth aspect, the biomarker monitoring fitness system of the seventh aspect or any other aspect, wherein the particular interval is 15 minutes.

According to a ninth aspect, the biomarker monitoring fitness system of the seventh aspect or any other aspect, wherein the particular interval is 1 minute.

According to a tenth aspect, the biomarker monitoring fitness system of the seventh aspect or any other aspect, wherein the determining the glucose exposure for the particular hour includes adding the average glucose level for the particular hour to a summation of average glucose levels of the patient for hours preceding the particular hour in a 24-hour period. According to an eleventh aspect, the biomarker monitoring fitness system of the tenth aspect or any other aspect, wherein the 24-hour period begins at midnight.

According to a twelfth aspect, the biomarker monitoring fitness system of the eleventh aspect or any other aspect, wherein: A) the particular interval is 15 minutes; B) the particular hour is 9:00 AM and defined by 60 minutes between 8:01 AM to 9:00 AM; C) determining the average glucose level for 8:01 AM to 9:00 AM by averaging one or more glucose readings received every 15 minutes during the particular hour; D) determining the glucose exposure for 8:01 AM to 9:00 AM includes adding the average glucose level for 8:01 AM to 9:00 AM to a summation of average glucose levels of the patient from midnight until 8:00 AM; and E) determining the target glucose exposure for 8:01 AM to 9:00 AM includes multiplying the glucose exposure limit per hour by 9. According to a thirteenth aspect, the biomarker monitoring fitness system of the first eleventh or any other aspect, wherein the wearable computing device is operatively connected to a GPS system for tracking a patient's movement.

According to a fourteenth aspect, the biomarker monitoring fitness system of the thirteenth aspect or any other aspect, wherein the wearable computing device is configured to display information associated with the patient's movement.

According to a fifteenth aspect, the biomarker monitoring fitness system of the fourteenth aspect or any other aspect, wherein the wearable computing device is configured to provide recommendations for meeting the glucose exposure limit based on the glucose exposure for the particular hour and the information associated with the patient's movement.

According to a sixteenth aspect, the biomarker monitoring fitness system may include a wearable computing device wirelessly connected to a sensor including a filament interacting with interstitial fluid and including: a display; and an integration module configured to synchronize glucose data received from the sensor and additional biomarker data; and configured for: A) deobfuscating glucose data received from the sensor on a particular interval; B) determining a glucose exposure for a particular hour based on the glucose data received on the particular interval; C) determining a target glucose exposure for the particular hour by multiplying a glucose exposure limit per hour by a numerical representation of a time at an end of the particular hour; D) integrating the glucose exposure for the particular hour and the additional biomarker data via the integration module for display; and E) displaying the glucose exposure for the particular hour as a proportion of the target glucose exposure for the particular hour and the additional biomarker data on the display.

According to a seventeenth aspect, the biomarker monitoring fitness system of the sixteenth aspect or any other aspect, the wearable computing device is configured for measuring the additional biomarker data including one or more of cardiovascular, pulmonary, and perspiratory data.

According to an eighteenth aspect, the biomarker monitoring fitness system of the sixteenth aspect or any other aspect, wherein deobfuscating glucose data includes decrypting the glucose data.

According to a nineteenth aspect, the biomarker monitoring fitness system of the eighteenth aspect or any other aspect, wherein the glucose data includes a glucose reading taken from the filament interacting with interstitial fluid.

According to a twentieth aspect, the biomarker monitoring fitness system of the nineteenth aspect or any other aspect, wherein the wearable computing device is configured for transmitting the glucose data and an identifier associated with the patient to a remote server.

According to a twenty-first aspect, the biomarker monitoring fitness system of the twentieth aspect or any other aspect, wherein the glucose data includes the identifier.

According to a twenty-second aspect, the biomarker monitoring fitness system of the twentieth aspect or any other aspect, wherein the wearable computing device associates the identifier with the received glucose data.

According to a twenty-third aspect, the biomarker monitoring fitness system of the nineteenth aspect or any other aspect, wherein the wearable computing device is configured for determining an average glucose level for the particular hour by averaging one or more glucose readings received on the particular interval during the particular hour.

According to a twenty-fourth aspect, the biomarker monitoring fitness system of the twenty-third aspect or any other aspect, wherein the particular interval is 15 minutes.

According to a twenty-fifth aspect, the biomarker monitoring fitness system of the twenty-third aspect or any other aspect, wherein the particular interval is 1 minute.

According to a twenty-sixth aspect, the biomarker monitoring fitness system of the twenty-third aspect or any other aspect, wherein the determining the glucose exposure for the particular hour includes adding the average glucose level for the particular hour to a summation of average glucose levels of the patient for hours preceding the particular hour in a 24-hour period.

According to a twenty-seventh aspect, the biomarker monitoring fitness system of the twenty-sixth aspect or any other aspect, wherein the 24-hour period begins at midnight.

According to a twenty-eighth aspect, the biomarker monitoring fitness system of the twenty-seventh aspect or any other aspect, wherein: A) the particular interval is 15 minutes; B) the particular hour is 9:00 AM, from 8:01 AM to 9:00 AM; C) determining the average glucose level for 8:01 AM to 9:00 AM by averaging one or more glucose readings received every 15 minutes during the particular hour; D) determining the glucose exposure for 8:01 AM to 9:00 AM includes adding the average glucose level for 8:01 AM to 9:00 AM to a summation of average glucose levels of the patient from midnight until 8:00 AM; and E) determining the target glucose exposure for 8:01 AM to 9:00 AM includes multiplying the glucose exposure limit per hour by 9.

According to a twenty-ninth aspect, the biomarker monitoring fitness system of the twenty-seventh aspect or any other aspect, wherein the wearable computing device is operatively connected to a GPS system for tracking a patient's movement.

According to a thirtieth aspect, the biomarker monitoring fitness system of the twenty-ninth aspect or any other aspect, wherein the wearable computing device is configured to display information associated with the patient's movement.

According to a thirty-first aspect, the biomarker monitoring fitness system of the thirtieth aspect or any other aspect, wherein the wearable computing device is configured to provide recommendations for meeting the glucose exposure limit based on the glucose exposure for the particular hour and the information associated with the patient's movement.

Both the brief overview and the following detailed description provide examples and are explanatory only. Accordingly, the brief overview and the following detailed description should not be considered to be restrictive. Further, features or variations may be provided in addition to those herein. For example, embodiments may be directed to various feature combinations and sub-combinations described in the detailed description.

BRIEF DESCRIPTION OF THE DRAWINGS

Furthermore, the drawings and brief descriptions below may contain text or captions that may explain certain embodiments of the present disclosure. This text is included for illustrative, non-limiting, explanatory purposes of certain embodiments detailed in the present disclosure. In the drawings:

FIG. 8A a flow chart of an exemplary glucose exposure process, according to one embodiment of the present disclosure;

DETAILED DESCRIPTION

Figure 1:
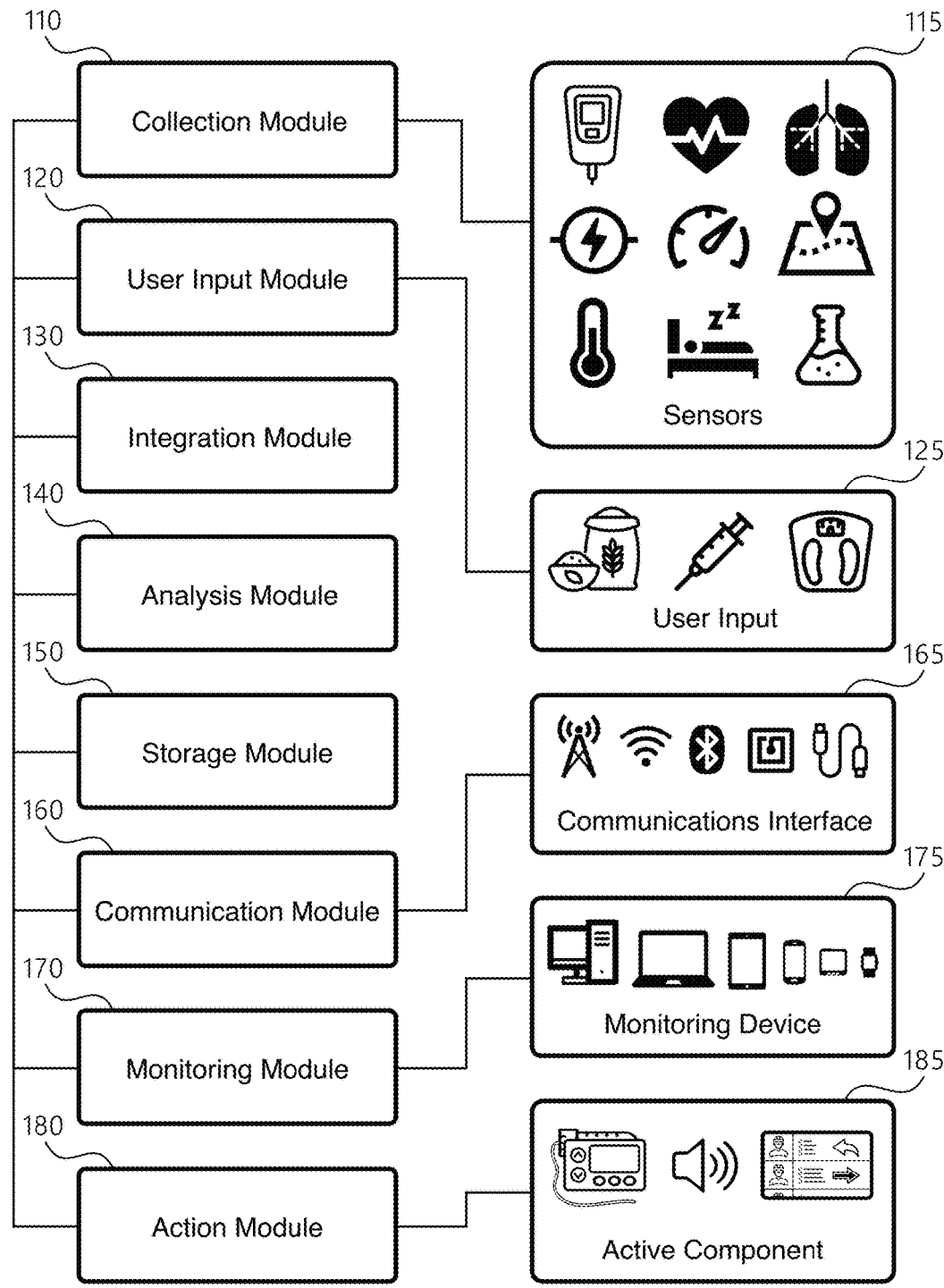
FIG. 1 illustrates an exemplary block diagram of a biomarker monitoring fitness system in accordance with various embodiments of the present disclosure.

As a preliminary matter, it will readily be understood by one having ordinary skill in the relevant art that the present disclosure has broad utility and application. As should be understood, any embodiment may incorporate only one or a plurality of the above-disclosed aspects of the disclosure and may further incorporate only one or a plurality of the above-disclosed features. Furthermore, any embodiment discussed and identified as being "preferred" is considered to be part of a best mode contemplated for carrying out the embodiments of the present disclosure. Other embodiments also may be discussed for additional illustrative purposes in providing a full and enabling disclosure. Moreover, many embodiments, such as adaptations, variations, modifications, and equivalent arrangements, will be implicitly disclosed by the embodiments described herein and fall within the scope of the present disclosure.

Accordingly, while embodiments are described herein in detail in relation to one or more embodiments, it is to be understood that this disclosure is illustrative and exemplary of the present disclosure, and are made for the purposes of providing a full and enabling disclosure. The detailed disclosure herein of one or more embodiments is not intended, nor is to be construed, to limit the scope of patent protection afforded in any claim of a patent issuing here from, which scope is to be defined by the claims and the equivalents thereof. It is not intended that the scope of patent protection be defined by reading into any claim a limitation found herein that does not explicitly appear in the claim itself.

Thus, for example, any sequence(s) and/or temporal order of steps of various processes or processes that are described herein are illustrative and not restrictive. Accordingly, it should be understood that, although steps of various processes or processes may be shown and described as being in a sequence or temporal order, the steps of any such processes or processes are not limited to being carried out in any particular sequence or order, absent an indication otherwise. Indeed, the steps in such processes or processes generally may be carried out in various different sequences and orders while still falling within the scope of the present disclosure. Accordingly, it is intended that the scope of patent protection is to be defined by the issued claim(s) rather than the description set forth herein.

Additionally, it is important to note that each term used herein refers to that which an ordinary artisan would understand such term to mean based on the contextual use of such term herein. To the extent that the meaning of a term used herein—as understood by the ordinary artisan based on the contextual use of such term—differs in any way from any particular dictionary definition of such term, it is intended that the meaning of the term as understood by the ordinary artisan should prevail.

Furthermore, it is important to note that, as used herein, "a" and "an" each generally denotes "at least one," but does not exclude a plurality unless the contextual use dictates otherwise. When used herein to join a list of items, "or" denotes "at least one of the items," but does not exclude a plurality of items of the list. Finally, when used herein to join a list of items, "and" denotes "all of the items of the list."

The following detailed description refers to the accompanying drawings. Wherever possible, the same reference numbers are used in the drawings and the following description to refer to the same or similar elements. While many embodiments of the disclosure may be described, modifications, adaptations, and other implementations are possible. For example, substitutions, additions, or modifications may be made to the elements illustrated in the drawings, and the processes described herein may be modified by substituting, reordering, or adding steps to the disclosed processes. Accordingly, the following detailed description does not limit the disclosure. Instead, the proper scope of the disclosure is defined by the appended claims. The present disclosure contains headers. It should be understood that these headers are used as references and are not to be construed as limiting upon the subjected matter disclosed under the header.

The present disclosure includes many aspects and features. Moreover, while many aspects and features relate to, and are described in, the context of biomarker monitoring fitness systems, embodiments of the present disclosure are not limited to use only in this context. Rather, any context in which blood glucose data may be measured, monitored, processed, or visualized in accordance to the various processes and systems described herein may be considered within the scope and spirit of the present disclosure.

I. Overview

This overview is provided to introduce a selection of concepts in a simplified form that are further described below. This overview is not intended to identify key features or essential features of the claimed subject matter. Nor is this overview intended to be used to limit the claimed subject matter's scope.

Embodiments of the present disclosure may provide processes, systems, and devices (collectively referred to herein as a "biomarker monitoring fitness system" or "system" 100) for monitoring various biomarkers, including lactate, ketone, blood glucose levels, and integrating such biomarker data with other data and systems.

a. Figure Overview

FIG. 1 shows a block diagram of an exemplary biomarker monitoring fitness system 100. In various embodiments, the system 100 may include a monitoring array including various sensors 115, of which one or more may be a continuous biomarker monitoring sensor, such as a sensor that continuously monitors glucose, lactate, and/or ketones, a user input element 125 such as a physical or virtual button for indicating carbohydrate intake, a communications interface 165 such as a Bluetooth or WiFi radio, a monitoring device 175 such as a smartwatch, tablet, mobile device, tablet, laptop, server, or other computing device, an active component 185 such as a speaker or display for audible or visual indications or a delivery system such as an insulin pump, and various modules 110, 120, 130, 140, 150, 160, 170, 180 (as described in greater detail below) that may facilitate various data gathering, integration, storage, communication, analysis, data integration and action functions of system 100.

In multiple embodiments, sensors 115 may include a wide array of sensing and measuring devices, such as various positional, environmental, biosensors, biomarkers, blood glucose sensors (as described in greater detail below), food and fluid intake (e.g. carb, protein, fat content, fluid volume; such functionality may also in some embodiments be handled as a user input 125), geospatial, route, and temporal location information, position, velocity, acceleration, power, step/pedometer, electrocardiogram, heart rate, blood pressure, body temperature, breathing rate, blood oxygen, ketones, sodium, potassium, lactate, hydration (e.g. sweat conductivity analysis, pH, chemical analysis), ambient temperature, humidity, chemical (e.g. drug, protein, or metabolite presence), volumetric (e.g. volume of insulin dispensed, volume of water consumed from container), sleep (e.g. acoustic, brainwave, light), eye-tracking (e.g. indicia of attention, alertness, fatigue), and many others.

In several embodiments, a continuous biomarker sensor constituent of a monitoring array may measure biomarker levels, such as the blood glucose, lactate, or ketone levels of a user in a variety of modalities, such as circulatory (blood) or interstitial fluid emplacement, fluid-drawing, light-based, ultrasonic, external electromagnetic, thermal, etc. In one or more embodiments, a continuous biomarker sensor may embody a variety of form factors, including an adhesive skin patch, a strap (e.g. for the wrist), a collar or cuff, a coil, a flexible wrap, an article of jewelry or other wearable form factors, or ocular, oral, or implantable form factors. In at least one embodiment, the continuous biomarker sensor may be implanted into a user's body (e.g., a user's arm) so that the continuous biomarker sensor may measure the amount of glucose in the blood or interstitial fluid. In some embodiments, the continuous biomarker sensor may measure a voltage drop (or other suitable signal/measurement) in the user's blood or interstitial fluid that is representative of the amount of glucose. In one embodiment, the continuous biomarker sensor may produce an electronic signal for the measured voltage drop and associate an identifier and/or timestamp with the electronic signal. In many embodiments, the continuous biomarker sensor may obfuscate the electronic signal and associated identifier and/or timestamp, and transmit this data to the monitoring device 175 via the communications interface 165. In one or more embodiments, the continuous biomarker sensor may obfuscate the glucose data, which may include the electronic signal, associated identifier, and/or timestamp, via encryption, hashing algorithms, steganography, or other similar processes.

In multiple embodiments, once the continuous biomarker sensor transmits the obfuscated glucose data to the monitoring device 175, the monitoring device 175 may deobfuscate the glucose data. In many embodiments, biomarker monitoring fitness system 100 may thereafter utilize the integration module 130 and/or analysis module 140 to translate the electronic signal to an amount of glucose in the user's body.

In various embodiments, system 100 may include a wireless power component for inductive powering or maintaining operation of various components. In at least one embodiment, additionally or alternatively, system 100 may include other power harvesting modalities such as thermal, motion, piezo, or solar.

Figure 2:
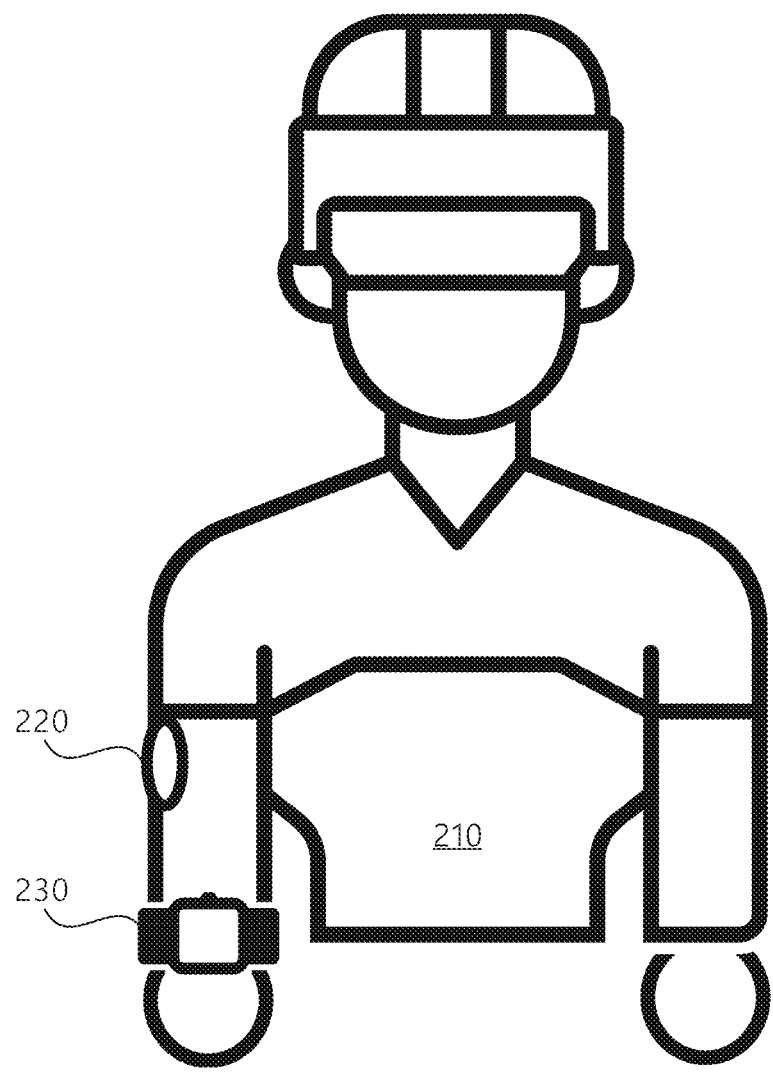
FIG. 2 illustrates an exemplary configuration of a biomarker monitoring fitness system in accordance with various embodiments of the present disclosure.

Referring now to FIG. 2, according to one embodiment, there is shown an exemplary user 210 outfitted with a continuous biomarker sensor 220 and display device 230. In many embodiments, user 210 may be, for example, an athlete such as a cyclist, and continuous biomarker sensor 220 and display device 230 may, as depicted, be sufficiently low-profile and securable as to permit endurance sport participation, weightlifting, or kayaking, and other like exercises. In one or more embodiments, the biomarker sensor 220 and/or display device 230 may include one or more of the sensors 115, including but not limited to a glucose sensor. In at least one embodiment, the display device 230 may include the monitoring device 175, including but not limited to a wrist reader, smart watch, and other similar devices.

Figure 4A:
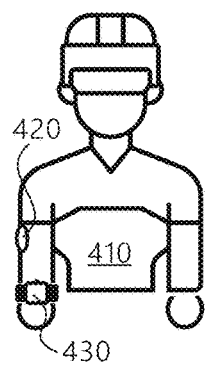
FIGS. 4A-C illustrate an exemplary utilization of a biomarker monitoring fitness system in accordance with various embodiments of the present disclosure.
Figure 4B:
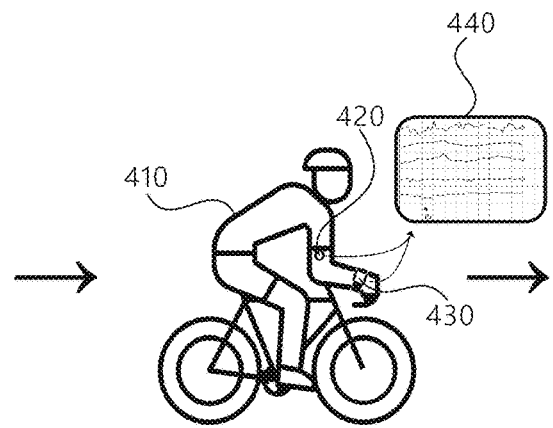
Figure 4C:
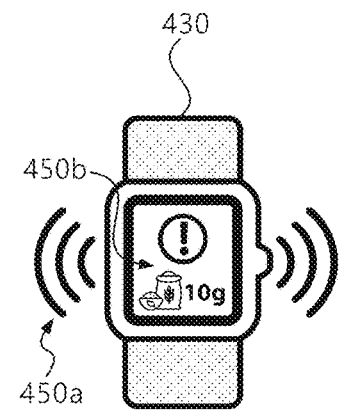

Referring now to FIGS. 4A-C, according to one embodiment, displaying various embodiments of the biomarker monitoring fitness system, there is shown an exemplary utilization of system 100 wherein a user 410 outfitted with a CGM sensor 420 and display device 430 may engage in physical activity (as depicted in FIG. 4B) and have monitored, by constituents of a monitoring array that may be present in CGM sensor 420, display device 430, and/or other elements, fitness data 440 corresponding to blood glucose levels and other signals. In one or more embodiments, user 420 may, as depicted in FIG. 4C, receive an audible alert 450a and/or visual alert 450b from display device 430 indicating an amount of carbohydrate is to be consumed, as predicted by system 100.

Figure 5:
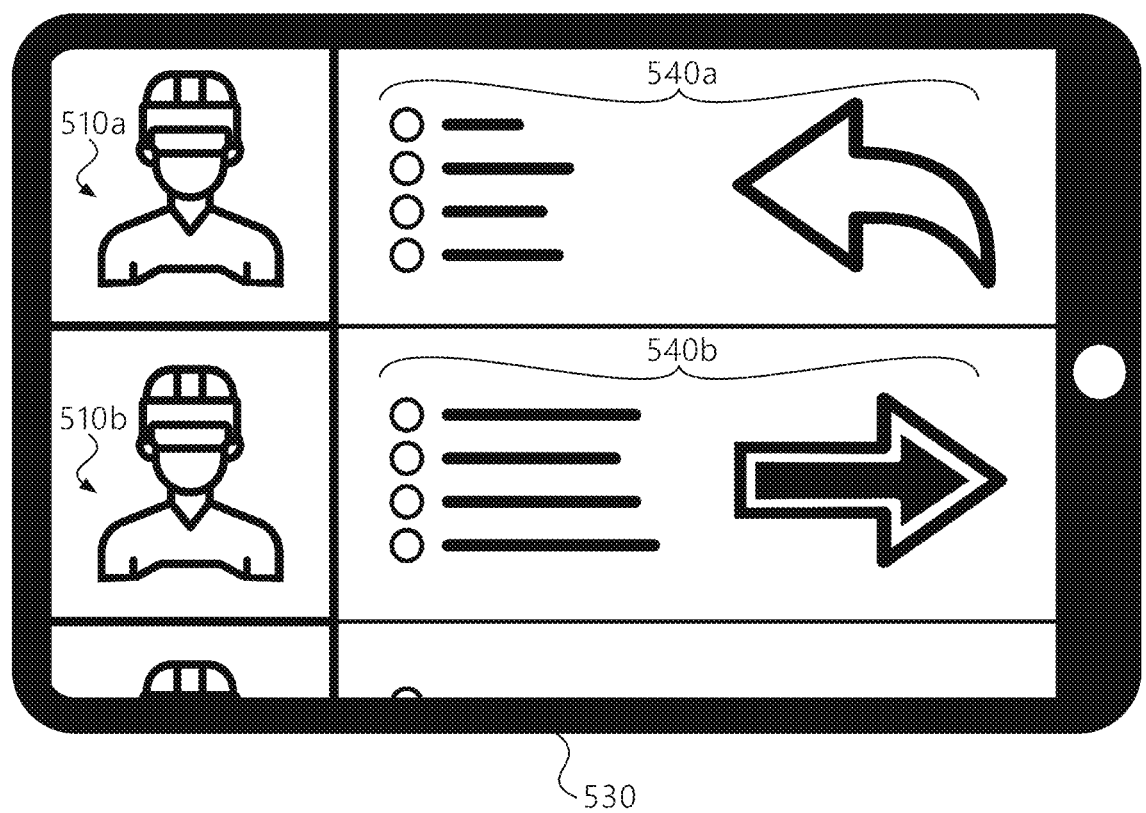
FIG. 5 illustrates an exemplary biomarker monitoring fitness system including a multi-user interface in accordance with various embodiments of the present disclosure.

Referring now to FIG. 5, according to one embodiment, there is shown the exemplary utilization of a display device 530 for monitoring fitness data of a plurality of users 510a-b, wherein each user 510a, 510b may have a monitoring array including a CGM sensor in operative communication with display device 530. In multiple embodiments, fitness data 540a, 540b of each such user 510a, 510b may be displayed by display device 530. For example, in one embodiment, the display device 530 may include the display of "actionable" data—which may be fitness data including blood glucose data gathered from the plurality of users 510a-b and/or generated by analysis module 140 based thereupon—such as indicating the advisability of line change in a hockey game, the need for carbohydrate intake of a cyclist, or the need to modify or discontinue a training session. Continuing with this example, in at least one embodiment, the display device 530 may provide for action by a user of the display device via user input, such as committing the line change, calling a "player safety" timeout or water break, signaling or executing a tactic that is communicated to users or their devices or equipment, modifying a parameter of a workout (e.g. reducing rowing or stationary bike resistance), or transmitting information to referees, trainers, or medical staff.

In various embodiments, the user of display device 530 may be a medical practitioner, and the plurality of users 510a-b may be on-location or remote recipients of medical care and/or monitoring. In one or more embodiments, users receiving remote care may provide for, e.g., efficient centralization and actionability of fitness data including blood glucose data for a plurality of users, monitoring of specialized feeding needs, or automated insulin delivery for users who are incapable of administering insulin themselves or for whom local monitoring and control of administration is prohibitive.

Figure 6:
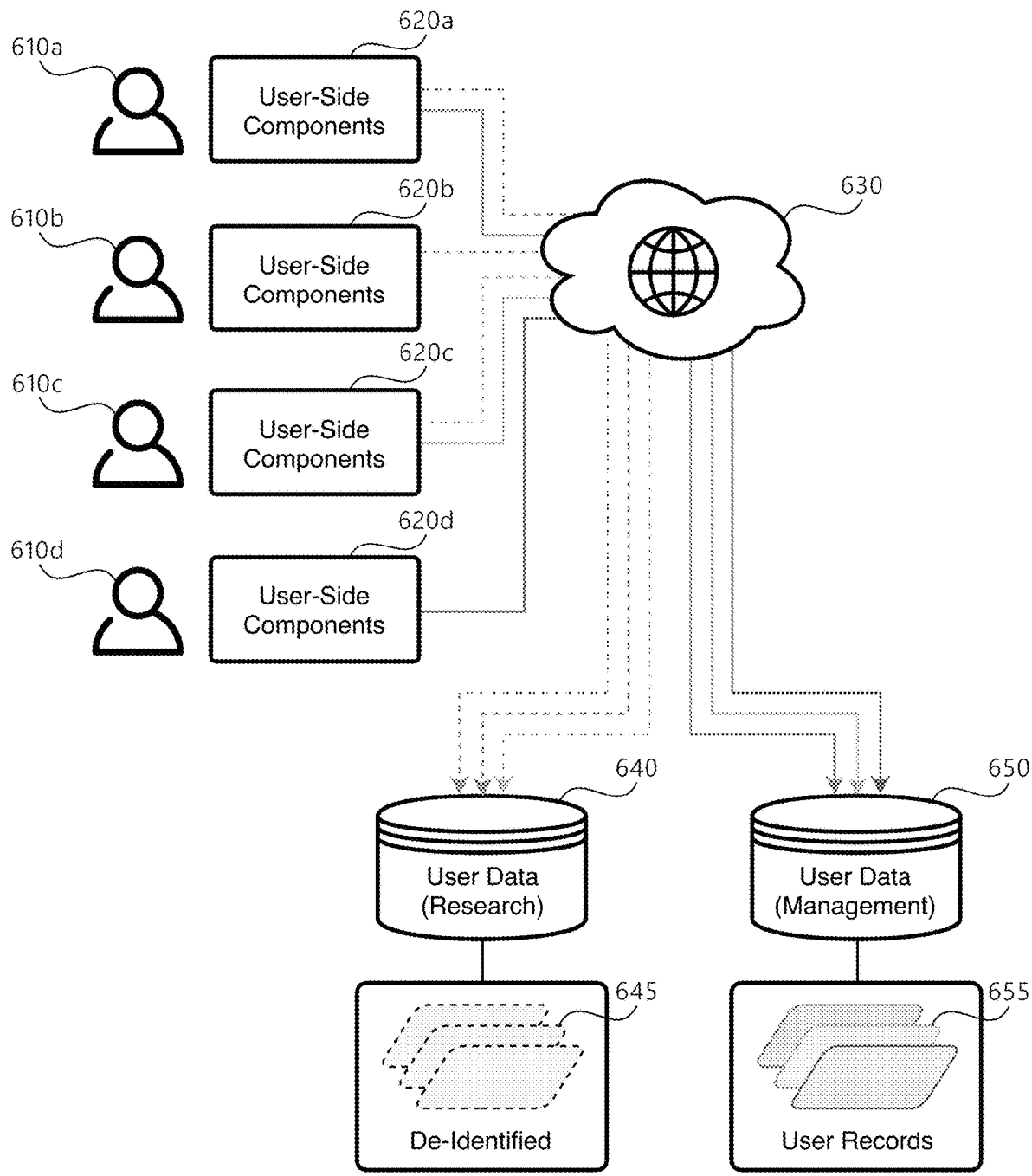
FIG. 6 illustrates an exemplary data flow diagram of a biomarker monitoring fitness system in accordance with various embodiments of the present disclosure.

Referring now to FIG. 6, there is shown an exemplary utilization of system 100 for gathering and managing fitness data of a plurality of users 610a-d. In many embodiments, system 100 may provide a mechanism whereby a user 610a, 610b, 610c, 610d may indicate, via a user-side component 620a, 620b, 620c, 620d (such as a monitoring device 175), to share de-identified user fitness data including blood glucose data (for example, for medical study) and transmit such deidentified data over a network 630 to a datastore 640 of de-identified user fitness data 645. In at least one embodiment, the system 100 may provide a mechanism whereby a user 610a, 610b, 610c, 610d may indicate, via a user-side component 620a, 620b, 620c, 620d (such as a monitoring device 175), to share identifiable user fitness data including blood glucose data (for example, in participating in a sport or fitness class) and transmit such identifiable user fitness data over a network 630 to a datastore 650 of identifiable user fitness data 655. For example, in one embodiment, a user might participate in de-identified sharing only (610b), identifiable sharing only (610d), both de-identified and identifiable sharing (610a, 610c), or neither de-identified nor identifiable sharing (not depicted).

In various embodiments, a user 610a may opt into the identifiable sharing system. In many embodiments, the identifiable sharing system may retrieve from the user's biomarker monitoring fitness system 100 stored personal identifiable information and data collected by sensors 115. In some embodiments, personal identifiable information may include the user's name, sex, age, height, weight, or any other information which may be used to identify the user. In one or more embodiments, the identifiable sharing system may allow the user 610a to opt out of sharing the user's name. In at least one embodiment, the identifiable sharing system may transmit identifiable user fitness data 655 to a centralized system, to a coach, display the identifiable user fitness data 655 on a monitor, and/or store the identifiable user fitness data 655. In a further embodiment, the identifiable user fitness data 655 may be used as training sets for machine learning algorithms that may recommend 24 hour glucose amounts for users for losing weight or for carbohydrate intake in preparation for physical activity. For example, in one embodiment, a user may opt into the identifiable sharing system for a fitness class, and the identifiable sharing system may retrieve and transmit the identifiable user fitness data 655 to a coach or medical practitioner for further analysis.

In multiple embodiments, a user 610a may opt into a de-identified sharing system. In some embodiments, the de-identifiable sharing system may retrieve, from the user's biomarker monitoring fitness system 100, stored data collected by sensors 115, but no personally identifiable information. In another embodiment, the de-identifiable sharing system may retrieve some user information to provide some context to the de-identified user fitness data 645, such as a user's height, weight, age, and/or gender, but may not make the user information public. For example, in one embodiment, a user 610a may opt into a de-identified sharing system, and the de-identified sharing system may retrieve de-identified user fitness data 645, which may include the user's glucose data, and other data collected by sensors 115, and also may retrieve a user's height, weight, gender, and/or age information, so that the de-identified user fitness data 645 may be associated with a height, weight, age, and/or gender. In a further embodiment, the de-identified user fitness data 645 and additional user information may be utilized in training machine learning algorithms for recommending glucose intake amounts to a user.

In several embodiments, the system may aggregate identifiable user fitness data 655 and/or de-identified user fitness data 645 from multiple users. In one or more embodiments, the system may utilize the aggregated data as training sets for machine learning algorithms, so that the system may make learned recommendations to the user. In many embodiments, the system may compare a user's fitness data to other users' fitness data based on similarities of user information, including but not limited to a user's height, weight, age, or gender. In at least one embodiment, learned recommendations may include a 24 hour glucose limit or goal for the user, a notification or message to the user to eat a low-carbohydrate meal or for the user to exercise (if the user's glucose is high), administering medication to the user, including but not limited to, insulin, weight loss medication, pre-diabetes medication, or medication to treat nonalcoholic steatohepatitis (NASH), or a notification or message to the user to eat a snack or meal that is high in carbohydrates (if the user's glucose is low), or a notification or message to the user to call an emergency medical provider because the user's glucose is severely low or high. In a further embodiment, the system may communicate with an emergency medical provider upon the user's glucose dropping below or rising above certain glucose amounts. For example, in one embodiment, a user may be a 40 year old male that is trying to lose weight, and the system may utilize the aggregated data to determine a 24 hour glucose limit for the user based on, at least, the 24 hour glucose amounts for male users in a similar age range that have lost weight or are at a lower weight than the user.

b. Applications

In various embodiments, applications of a biomarker monitoring fitness system 100 may span a variety of fields, contexts, and use cases. In many embodiments, there are many circumstances in which features of biomarker monitoring, such as lactate, ketone, blood glucose, and carbohydrate intake monitoring, monitoring for fatigue, carbohydrate intake needs for physical activity, and diagnostic purposes, predictive carbohydrate intake needs for preparing for endurance based physical activity, predictive insulin delivery, and group blood glucose data collection may be advantageous.

i. Sports and Fitness

In multiple embodiments, system 100 may be advantageous in contexts such as training for endurance sports (e.g. cycling, running, marathon running, ultramarathons, swimming, triathlon, iron man), outdoor recreation (e.g. hiking, climbing, parkour, scuba diving), sports (e.g. soccer, football, baseball), dance, cheering, fitness classes, bootcamps, kickboxing, weight training, and cardio training.

ii. Medical

In several embodiments, system 100 may be advantageous in contexts such as medical facility patient monitoring (on-location and remote), screening for diabetes and pre-diabetes and crafting treatment plans therefor, automation of insulin delivery and other "closed loop" drug delivery systems, and medical study.

iii. Miscellaneous

In one or more embodiments, system 100 may be advantageous in contexts such as wearing for consistently better personal health information and assistance in decision-making (e.g. carbohydrate consumption), and the study and predictive modeling of blood glucose and carbohydrate consumption on longevity and mental acuity.

II. Platform Modules

Details with regards to each module is provided below. Although modules are disclosed with specific functionality, it should be understood that functionality may be shared between modules, split between modules, or duplicated by modules. Various modules may be embodied in one or more components, computing devices, or computing systems, and may be physical or virtual. The name of a module should not be construed as limiting upon the functionality of the module. Modules may reference, be referenced by, or be disclosed in the context of or in reference to processes or steps thereof at various points in the present disclosure, and such should not be construed as limiting upon the functionality of the module.

a. Collection Module 110

In some embodiments, collection module 110 may facilitate data collection by sensors 115 such as a continuous biomarker sensor, including but not limited to, a lactate sensor, ketone sensor, CGM sensor, power meter, heart rate monitor, blood oxygen sensor, gyroscope, illuminance sensor, body temperature sensor, or ambient temperature sensor. In one or more embodiments, the collection module 110 may automatically or substantially automatically tracks carbohydrate intake (e.g. RFID-assisted).

b. User Input Module 120

In many embodiments, user input module 120 may collect the input of user input 125 such as manual input of biometric data (e.g. height, weight, age, sex), event data (e.g. indicating an intake of carbohydrates or a manual delivery of a drug such as insulin), and parameters of a course of activity (e.g. distance, path, time of day, lap time, weight or model of equipment). In at least one embodiment, system 100 may facilitate user input 125 via physical means such as button, dial, mouse, keyboard, trackpad, and sensors like piezo, voice, or motion sensors, as well as virtual means such as graphical user interface buttons and other elements that may be interacted with via a physical means as above, touch-screen, etc.

c. Integration Module 130

In several embodiments, integration module 130 may facilitate the synchronization of data which may variously include data collected by sensors 115 and generally collection module 110, data received from user input 125 and generally user input module 120, and external data received by communications interface 165 and generally communication module 160. In one or more embodiments, integration module 130 may, alternatively or in addition, facilitate the integration, interoperability, formatting, or collation of system 100 fitness data with various health, fitness, GIS, and communication data protocols, formats, and APIs, such as Health Level-7 (HL7), openEHR, Ambulatory Glucose Profile (AGP), Flexible & Interoperable Data Transfer (FIT) protocol, GeoJSON, GPS exchange format (GPX), and various other XML, JSON, CSV, blockchain, proprietary, etc. protocols and systems. For example, in some embodiments, data collected by sensors 115 is formatted and logged into a .FIT file such that the user's activity details and sensed data can be integrated and viewed through various health, fitness, GIS, and communication platforms, such as Garmin, Strava, TrainingPeaks, Runkeeper, and others. In at least one embodiment, data collected by sensors 115 includes sensed data relating to biomarker levels, such as ketone, sodium, potassium, lactate, and/or glucose levels, which is formatted and logged into a .FIT file (or other file type) such that the user's sensed biomarker data can be integrated and viewed through the various health, fitness, GIS, and communication platforms.

In various embodiments, the user's sensed biomarker data may be used to show, for example, the user's blood glucose level or exposure. In one or more embodiments, the user's blood glucose level may be the user's current blood glucose level or the user's total blood glucose exposure for the day. In at least one embodiment, the user's total blood glucose exposure for the day may be a running total of the user's blood glucose amounts over the course of a day. For example, in one embodiment, the user's sensed biomarker data may be utilized by the biomarker monitoring fitness system 100 to calculate the user's blood glucose amount every hour throughout the day, and add each measurement at every hour to the previous measurements, and display the running total of blood glucose amounts. In a further embodiment, biomarker monitoring fitness system 100 may compare the running total of blood glucose amounts to a 24 hour blood glucose target or limit. In an even further embodiment, the 24 hour blood glucose target or limit may be measured per hour, so that the display may indicate to the user if the user's blood glucose level from the previous hour is more than or less than the blood glucose target or limit for the previous hour.

d. Analysis Module 140

In many embodiments, analysis module 140 may facilitate the predictive functionality of system 100 with respect to fitness data including biomarker levels, such as ketone levels, lactate levels, and/or blood glucose levels and user needs (e.g., carbohydrate intake for physical activity, insulin delivery, etc.). In some embodiments, analysis module 140 may include artificial intelligence, machine learning, neural network, etc. systems for training on user fitness data and applying this training to make predictions based on further user fitness data. In one or more embodiments, analysis module 140 may or may not systematically, temporally, or physically (in the computing device sense) separate training and inference operations. In additional embodiments, analysis module 140 may perform some training and/or predictive operations on a remote server, a cloud computing platform, a user's device, and so forth.

In various embodiments, analysis module 140 may be trained to predict, based on user fitness data including biomarker levels, such as ketone levels, lactate levels, and/or blood glucose levels, the need for carbohydrate consumption, an insulin delivery event, or other types of events. In many embodiments, analysis module 140 may be trained to predict, based on user fitness data including biomarker levels, blood glucose levels, optima and maxima of exertion (distance, weight, etc.) given certain criteria, whether a user can safely undertake (or maintain) a course of physical activity, or a carbohydrate loading tactic.

In some embodiments, analysis module 140 may facilitate the operation of a closed loop drug delivery system that includes, for example, an insulin pump, whereby monitoring and delivery devices and feedback therefrom are integrated to enable continuously self-correcting insulin delivery without the need for user monitoring or user direction to deliver insulin. In one or more embodiments, the insulin delivered to the user may be rapid-acting insulin, short-acting insulin, intermediate-acting insulin, mixed insulin, and long-acting insulin. In at least one embodiment, the analysis module 140 may determine, based on the severity of blood glucose level increases or decreases and other factors, the type of insulin to deliver to the user.

In multiple embodiments, analysis module 140 may also notify the user to ingest or otherwise administer to the user, medication based on the fitness data. In some embodiments, the medication may include one or more class of drugs to treat nonalcoholic steatohepatitis (NASH), one or more class of drugs for weight reduction, and/or one or more drugs to treat pre-diabetic conditions such that the user does not become diabetic.

e. Storage Module 150

In multiple embodiments, storage module 150 may facilitate the storage of fitness data by system 100. In many embodiments, storage module 150 may store data locally, as in the flash memory of a mobile device or storage unit of a smart sensor device, remotely on a user device such as a laptop or tablet, remotely in a cloud-based storage medium, or a combination of the above.

f. Communications Module 160

In several embodiments, communications module 160 may facilitate communications over a variety of networking modalities, such a WiFi, Bluetooth, cellular data, near field communication (as with a device such as an insulin pen), RFID, electromagnetic induction, infrared, optical, sonic, wired or otherwise direct electrical connection, and so forth. In some embodiments, communications module 160 may facilitate communications between components of system 100 and/or external systems and sources, such as GPS satellite infrastructure, time synchronization servers, data repositories, external fitness and sporting venue systems, and so forth. In at least one embodiment, communications module 160 may include "internet of things" connectivity between elements—for example, between a CGM sensor, a smartwatch, and a volume tracking dispenser of a smart water bottle.

g. Monitoring Module 170

In various embodiments, monitoring module 170 may facilitate the display of and interaction with fitness data by a monitoring device 175, such as a mobile device, a dedicated fitness tracking device, a vehicular display, a flexible display, an e-paper display, a heads-up display, a medical device display, a virtual reality or augmented reality display (e.g. a headset, glasses, contacts), a projective or holographic display system, a paper tape (e.g. EKG paper), or one or more lights (e.g. an LED indicator or metering array).

In some embodiments, monitoring module 170 may provide a multi-line chart depicting user fitness data over time in a manner similar to the depiction in FIG. 4B. In one embodiment, system 100 may include a plurality of monitoring devices 175.

h. Action Module 180

In multiple embodiments, action module 180 may facilitate one or more indications to a user or device or system of the user. For example, in some embodiments, an active component 185 such as a speaker may provide a user with audible indication of a predictive carbohydrate intake event (e.g. a spoken command, such as "Consume 10 grams of carbs now."), a screen or indicator light may flash or provide information regarding or hydration needs, or a haptic feedback mechanism may vibrate a user's wrist (e.g. via a watch or fitness tracker device), hands (e.g. via a glove), or another part of the user's body (e.g. via an element of a diver's wetsuit). In many embodiments, more than one active component 185 may provide an indication for a single event, and a single active component 185 may provide indications for multiple types of events. For example, in one embodiment, action module 180 may provide a screen alert for a carbohydrate intake event as well as a screen alert for a "construction ahead" notification regarding the user's route.

III. Processes

The following are examples of processes of that may utilize or be performed by system 100. Various hardware and software components may be used at the various steps of operations disclosed with reference to processes and steps thereof. Although the steps of example processes are disclosed in a particular order, it should be understood that the order is disclosed for illustrative purposes only. Steps may be combined, separated, reordered, and various intermediary steps may exist. Accordingly, it should be understood that the various steps, in various embodiments, may be performed in arrangements that differ from the ones claimed below. Moreover, various steps may be added or removed without altering or deterring from the fundamental scope of the depicted processes and systems disclosed herein.

According to one embodiment, a process may be performed by at least one of modules 110, 120, 130, 140, 150, 160, 170, 180 (or any other components discussed herein). In various embodiments, a process may be embodied as, for example, but not limited to, executable machine code, which when executed, performs a process.

Steps disclosed can be considered independently without the context of the other steps within the same process or different processes, and within the same module or different modules. Each step may contain language defined in other portions of this specifications. Each step disclosed for one module may be mixed with the operational steps of another module. In the present disclosure, each step can be claimed on its own and/or interchangeably with other steps of other modules.

Figure 3:
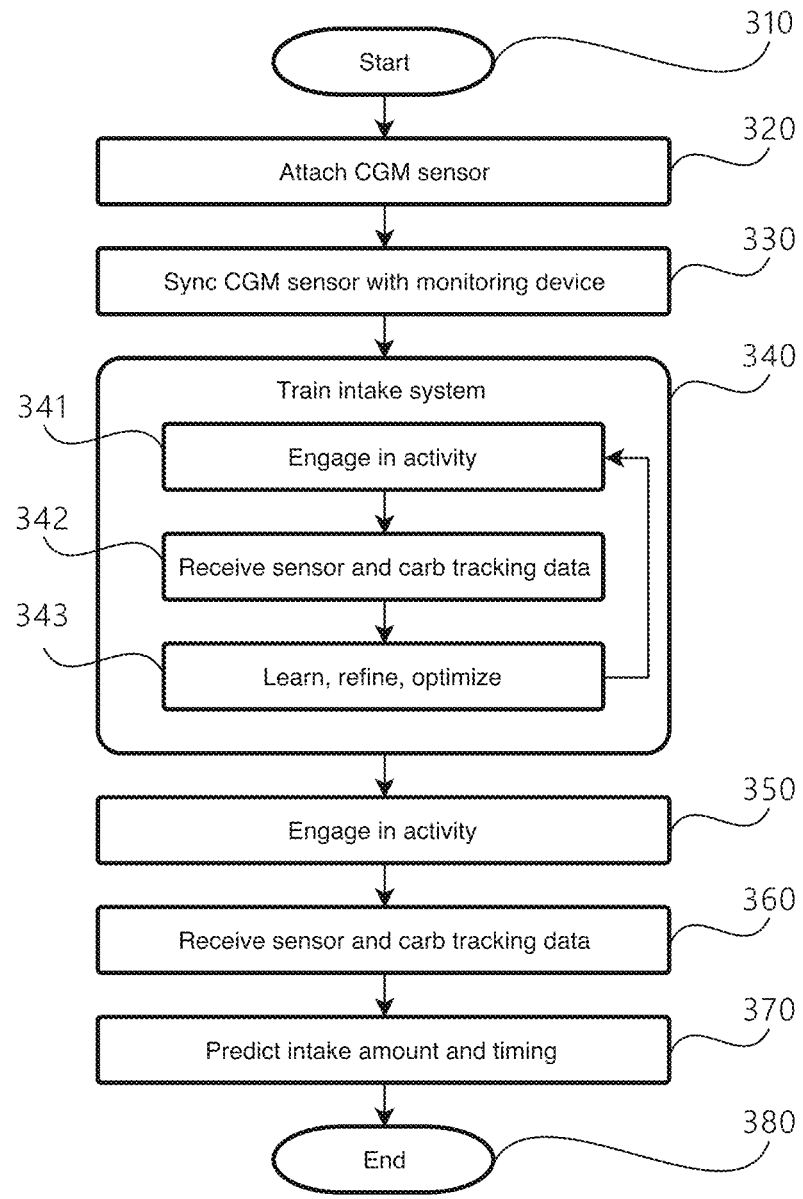
FIG. 3 illustrates an exemplary process for using a biomarker monitoring fitness system in accordance with various embodiments of the present disclosure.

Referring now to FIG. 3, there is shown an exemplary process 300 for utilizing a biomarker monitoring fitness system 100 in accordance with various embodiments of the present disclosure.

According to one embodiment, at step 310, process 300 may begin.

In some embodiments, at step 320, a monitoring array including continuous biomarker monitoring, such as continuous lactate, ketone, and/or glucose monitoring functionality may be attached to a user. In one embodiment, a CGM sensor such as the Abbott Laboratories Freestyle Libra® device may be attached to the body of the user.

In several embodiments, at step 330, a wearable computing device may be placed in operative communication (or "synced") with the monitoring array. In at least one embodiment, the wearable computing device operatively connected with the monitoring array may also include a fitness tracking device (such as, e.g., the Wahoo ELEMNT BOLT®). In a further embodiment, the wearable computing device may include one or all constituents of the monitoring array. For example, in one embodiment, sensors and monitoring may all be present on a single device.

In multiple embodiments, at step 340, an intake system may be trained. In some embodiments, analysis module 140 may include the intake system. In one embodiments, step 340 may include machine learning processes. In at least one embodiment, training and inference operations may be performed by the same user-local device(s) that perform fitness data collection operations. In another embodiment, one or both of training and inference operations may be performed remotely (e.g. via a cloud computing platform) from the user-local device(s) that perform fitness data collection operations. In one or more embodiments, step 340 may include substeps such as steps 341, 342, and 343, which may be performed iteratively.

In various embodiments, at substep 341 (which may occur concurrently and/or iteratively with other substeps in this step), the user may engage in an activity while the monitor array is attached and system 100 is gathering (via, e.g., collection module 110) data therefrom. In many embodiments, the activity may be a physical activity or may be a user's normal day-to-day activities, such as but not limited to working, running errands, etc.

In several embodiments, at substep 342 (which may occur concurrently and/or iteratively with other substeps in this step), throughout the activity, fitness data may be gathered by system 100, which fitness data may include sensor data from the monitoring array (e.g. ketone, lactate, and/or blood glucose levels), gathered continuously and/or at regular intervals, as well as carbohydrate intake tracking data (via, e.g., user input 125 or one or more sensors 115). For example, in one embodiment, consistent with step 340 and the substeps thereof, a user may begin an activity (e.g., running), consume an amount of carbohydrates (e.g. a 20 g gummy), and indicate to the system 100 (via, e.g., a carb tracking button on the monitoring device) that this amount has been consumed. In some embodiments, sensor module 110 may be concurrently gathering data from sensors 115 throughout the run.

In multiple embodiments, at substep 343 (which may occur concurrently and/or iteratively with other substeps in this step), the intake system (e.g. analysis module 140) may employ one or multiple machine learning steps or modalities to generate predictive models. In some embodiments, learning, refining, and optimizing may be achieved by training the intake system based on fitness data of the user and, optionally, fitness data of other users. In one or more embodiments, substep 343 may include modeling, based on time, activity, and measured blood glucose levels, the optimization of blood glucose levels and the needed carbohydrate intake amounts and timings for a course of activity. In one embodiment, such optimization may approach carbohydrate need from instant and/or future looking (i.e. "whole course" or training) perspectives.

In some embodiments, at step 350, the user may engage in an activity, for example a bike ride or working at the user's place of employment, and at step 360, system 100 may receive fitness data related to this activity.

In various embodiments, at step 370, system 100 may generate a prediction, based upon one or more predictive models (e.g. as trained in step 340) and fitness data including blood glucose levels related to this activity, of the timing and amount of carbohydrate intake. In one or more embodiments, an indication such as a visual indication (e.g. text, graphics, illumination, color change) and/or an auditory indication (e.g. a tone, an alarm, spoken words) may be provided to the user to consume an amount of carbohydrates as predicted by system 100.

In multiple embodiments, the system 100 may determine that the user's current blood glucose levels are higher than the glucose needed for the activity. In one or more embodiments, the system 100 may indicate to the user to consume less carbohydrates as part of the user's next meal, exercise, drink water, and/or take insulin. For example, in one embodiment, the user may indicate to the system 100 that the user is at work, which includes sitting at a desk for long periods of time. Continuing with this example, the system 100 may provide to the user an amount of carbohydrates needed for the activity (working) as predicted by the system 100, and if the user intakes more glucose than needed, or the user's blood glucose is too high, the system may recommend to the user to eat a low-carb lunch (such as a salad) or to go for a walk for a certain amount of time, to lower the user's blood glucose levels.

In many embodiments, at step 380, process 300 may conclude.

The order of steps presented are only illustrative of the possibilities and those steps can be executed or performed in any suitable fashion. Moreover, the various features of the examples described here are not mutually exclusive. Rather any feature of any example described here can be incorporated into any other suitable example. It is intended that the specification and examples be considered as exemplary only, with a true scope and spirit of the systems and processes being indicated by the following claims.

IV. Platform Architecture

Embodiments of system 100 may include aspects including, but not limited to, mobile software applications (or "apps"), websites, web applications, desktop software, server software, embedded software, microcontrollers, databases, wired and wireless networking hardware and software, sensors (including chemical, biological, and environment sensors) and various computing devices. Moreover, in some embodiments, system 100 or aspects thereof may be hosted one or more physical or virtual servers, cloud computing services, blockchain platforms, or distributed computing platforms. Alternatively or in addition, system 100 may be implemented in one or more of a plurality of mobile devices.

Although processes disclosed herein have been described to be performed by a computing device 700, it should be understood that, in some embodiments, different operations may be performed by different networked elements in operative communication with computing device 700. Computing device 700 may include, but not be limited to, a desktop computer, a laptop, a server, a dedicated diagnostic device, a touchscreen, a tablet, or a mobile telecommunications device.

Embodiments of the present disclosure may include a system having a memory storage and a processing unit. The processing unit coupled to the memory storage, wherein the processing unit is configured to perform the steps of processes disclosed herein.

Figure 7:
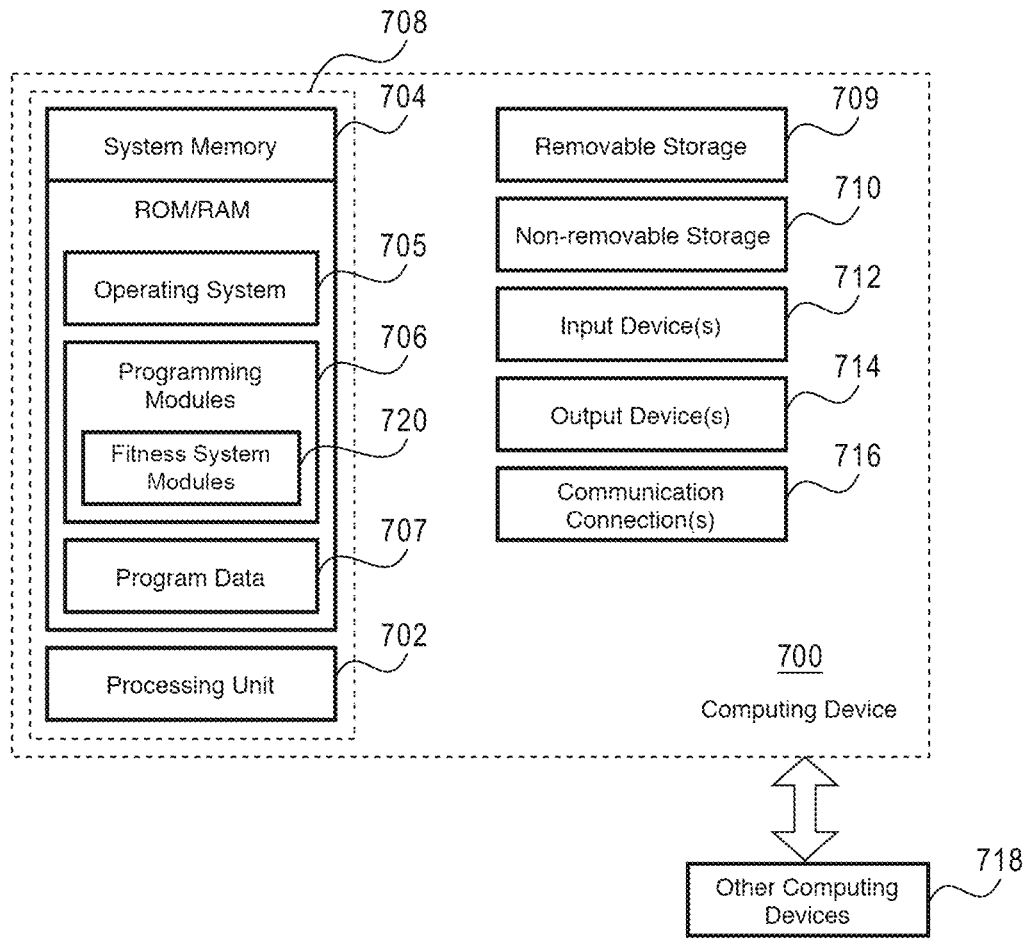
FIG. 7 illustrates an exemplary block diagram of a computing system for a biomarker monitoring fitness system in accordance with various embodiments of the present disclosure.

FIG. 7 illustrates an exemplary block diagram of a system including computing device 700, according to one embodiment of the present disclosure. In various embodiments, the aforementioned memory storage and processing unit may be implemented in a computing device, such as computing device 700 of FIG. 7. In one or more embodiments, any suitable combination of hardware, software, or firmware may be used to implement the memory storage and processing unit. For example, in one embodiment, the memory storage and processing unit may be implemented with computing device 700 or any of other computing devices 718, in combination with computing device 700. In some embodiments, the aforementioned system, device, and processors are examples and other systems, devices, and processors may include the aforementioned memory storage and processing unit, consistent with embodiments of the disclosure.

With reference to FIG. 7, an exemplary system consistent with an embodiment of the disclosure may include a computing device, such as computing device 700, according to one embodiment of the present disclosure. In multiple embodiments, in a basic configuration, computing device 700 may include at least one processing unit 702 and a system memory 704. In some embodiments, depending on the configuration and type of computing device, system memory 704 may include, but is not limited to, volatile (e.g. random access memory (RAM)), non-volatile (e.g. read-only memory (ROM)), flash memory, or any combination. In many embodiments, system memory 704 may include operating system 705, one or more programming modules 706 (including, for example, fitness system modules 720), and may include a program data 707. In one or more embodiments, operating system 705, for example, may be suitable for controlling the operation of computing device 700. In at least one embodiment, features of programming modules 706 may include formatting and displaying information to the user, and formulating and transmitting programming instructions. Furthermore, embodiments of the disclosure may be practiced in conjunction with a graphics library, other operating systems, or any other application program and is not limited to any particular application or system. In one embodiment, this basic configuration is illustrated in FIG. 7 by those components within a dashed line 708.

In various embodiments, computing device 700 may have additional features or functionality. For example, in some embodiments, computing device 700 may also include additional data storage devices (removable and/or non-removable) such as, for example, magnetic disks, optical disks, or tape. In one or more embodiments, such additional storage is illustrated in FIG. 7 by a removable storage 709 and a non-removable storage 710. In at least one embodiment, computer storage media may include volatile and nonvolatile, removable and non-removable media implemented in any process or technology for storage of information, such as computer readable instructions, data structures, program modules, or other data. In many embodiments, system memory 704, removable storage 709, and non-removable storage 710 are all computer storage media examples (i.e., memory storage). In one embodiment, computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information and which can be accessed by computing device 700. In some embodiments, any such computer storage media may be part of device 700. In at least one embodiment, computing device 700 may also have input device(s) 712 such as a keyboard, a mouse, a pen, a sound input device, a touch input device, a camera, a sensor, etc. In many embodiments, output device(s) 714 such as a display, speakers, a printer, etc. may also be included. In one embodiment, the aforementioned devices are examples and others may be used.

In several embodiments, computing device 700 may also contain a communication connection 716 that may allow device 700 to communicate with other computing devices 718, such as over a network in a distributed computing environment, for example, an intranet or the Internet. In one or more embodiments, communication connection 716 is one example of communication media. In at least one embodiment, communication media may typically be embodied by computer readable instructions, data structures, program modules, or other data in a modulated data signal, such as a carrier wave or other transport mechanism, and includes any information delivery media. In some embodiments, the term "modulated data signal" may describe a signal that has one or more characteristics set or changed in such a manner as to encode information in the signal. In many embodiments, by way of example, and not limitation, communication media may include wired media such as a wired network or direct-wired connection, and wireless media such as acoustic, radio frequency (RF), infrared, and other wireless media. In one embodiment, the term computer readable media as used herein may include both storage media and communication media.

In various embodiments, as stated above, a number of programming modules 706 and data files may be stored in system memory 704, including operating system 705. In one or more embodiments, while executing on processing unit 702, programming modules 706 may perform processes including, for example, one or more of process steps as described above. In at least one embodiment, the aforementioned process is an example, and processing unit 702 may perform other processes. In one embodiment, other programming modules 706 that may be used in accordance with embodiments of the present disclosure may include mobile device applications, data visualization applications, authentication applications, data file formatting (e.g. GIS file format) applications, network communication applications, database applications, etc.

V. Glucose Exposure Process

In various embodiments, the present systems and processes determine glucose exposure for a particular user on an hourly basis. To do so, in at least one embodiment, the systems and processes determine average glucose for the user for each hour, then sum the average glucose per hour over the number of hours currently passed in a given day to determine a glucose exposure for the current time/hour (e.g., sums the average glucose from 12:00 AM-1:00 AM, 1:00 AM-2:00 AM, 2:00 AM-3:00 AM, and 4:00 AM-5:00 AM to determine a glucose exposure at 5:00 AM).

In order to determine an average glucose level for an hour, in at least one embodiment, the disclosed systems and processes: a) receive glucose data (e.g., a reading of current glucose levels of a user) from a sensor in predetermine intervals (e.g., 15 minutes); and b) averages the received glucose data over an hour (e.g., averages four glucose readings taken at 15 minute intervals over the hour).

In at least one embodiment, the present systems and processes display average glucose level for a particular hour as a percentage of a glucose target or limit for the day and/or hour (or a limit/target for a day thus far). In some embodiments, the systems and processes may create alerts based on current glucose exposure. For example, if a user's current glucose exposure is over the target or limit for the hour (e.g., thus far in the day), then the systems and processes may recommend that the user embark on glucose reducing or limiting actions (e.g., go for a walk, eat a low carb lunch, etc.). In this way, the systems and processes may enable a user to tweak habits or actions to influence glucose exposure during a day.

In at least one embodiment, the systems and processes may "backfill" glucose data for times when a sensor (e.g., that reads a user's glucose) is disconnected or glucose readings are otherwise unavailable (e.g., data could be corrupted, unavailable, or otherwise unusable) via one or more processes or mechanisms discussed herein.

For example, in one embodiment, a user (or the system) may set a glucose exposure limit of 1200 units of measurement (such as, e.g., milligrams per deciliter) per day. Based on the glucose exposure limit, the glucose exposure system may determine at a given time the target glucose limit for that given time, as well as the user's glucose exposure. Continuing with the above example, if the day begins at midnight (00:00 AM) and goes for 24 hours, then the glucose exposure limit per hour would be 50 mg/dl. If the user checks his glucose exposure at 8:00 AM, the target glucose exposure would be 400 milligrams, and the system 100 would display the user's glucose exposure for 8:00 AM (e.g., 390 mg/dl based on sensor readings, as discussed herein) compared to the target glucose for 8:00 AM, to indicate to the user if the user was below, at, or above the target glucose exposure limit for 8:00 AM.

Turning now to FIG. 8A, an exemplary glucose exposure process 800 is described, according to one embodiment of the present disclosure. In various embodiments, a user may first connect the continuous biomarker sensor 220 to the user's body, such that the continuous biomarker sensor 220 is interacting with the interstitial fluid or otherwise determining a level of glucose within the patient's blood. In one or more embodiment, the continuous biomarker sensor 220 may include, but is not limited to, a glucose monitor.

According to one embodiment, at step 802 of process 800, the system 100 may receive, facilitated by the communications interface 165, the obfuscated glucose data from the continuous biomarker sensor 220 at a particular interval. In at least one embodiment, the obfuscated glucose data is derived from the continuous biomarker sensor 220 interacting with the user, and specifically, with the user's blood or interstitial fluid. In one or more embodiments, the system 100 may receive the obfuscated glucose data at the monitoring device 175 via the communications interface 165.

In multiple embodiments, the particular interval is a time interval by which the system 100 receives the obfuscated glucose data from the continuous biomarker sensor 220. In many embodiments, the particular interval may one second, or may be one day, or any time therebetween. For example, in one embodiment, the particular interval may be 15 minutes, 30 minutes, 1 hour, 1 day, etc.

In several embodiments, the particular interval may be the time interval between the continuous biomarker sensor 220 conducting readings of the glucose in the user's body. In this embodiment, when the continuous biomarker sensor 220 conducts a reading of glucose data, the continuous biomarker sensor 220 may also record a timestamp and associate the time stamp with the received glucose data. Continuing in this embodiment, the continuous biomarker sensor 220 may thereafter transmit the glucose data and associated time stamp to the monitoring device 175 via the communications interface 165.

At step 804, in various embodiments, the system 100 may deobfuscate the obfuscated glucose data received from the continuous biomarker sensor 220. In one or more embodiments, the monitoring device 175, integration module 130, and/or the analysis module 140 may deobfuscate the obfuscated glucose data. As will be understood from discussions here, the continuous biomarker sensor 220 may obfuscate glucose data via encryption, hashing, steganography, etc. In some embodiments, once the monitoring device 175 receives the obfuscated (or encrypted) glucose via the communications interface 165, the monitoring device 175 may deobfuscate, decrypt, or otherwise decode the glucose data. In at least one embodiment, the monitoring device 175 may transmit the obfuscated to integration module 130 and/or the analysis module 140 for deobfuscation.

At step 806, in multiple embodiments, the system 100 may determine a glucose exposure over an interval of time based on the glucose data at the particular time interval. In several embodiments, the glucose exposure over the interval of time may be an average of the received glucose data at the particular interval over the course of the interval of time. In one or more embodiments, the interval of time may be the same amount of time as the particular interval, or may be a longer amount of time such that the glucose exposure may be based on more data. In at least one embodiment, the interval of time may be fifteen, thirty, or sixty minutes, a number of hours (see example below regarding a running total), or some other amount of time. For example, in one embodiment, the particular interval may be fifteen minutes, and the interval of time may be sixty minutes, such that the continuous biomarker sensor 220 receives glucose data four times within the interval of time. Continuing with this example, the received glucose data over the sixty minute interval of time may be 90, 92.5, 97.5, and 100 (in units of measurement), which averages to a glucose exposure of 95 units of measurement over the sixty minute interval of time (or average glucose level for the particular hour).

In a further embodiment, the system 100 may calculate a running total of glucose exposure through a twenty-four hour day by adding the determined glucose exposures (or average glucose level) over the intervals of time (or a single interval of time might be the time of the running total) throughout the twenty-four hours in a day. For example, in one embodiment, if the interval of time is sixty minutes, and the twenty-four hour day begins at midnight (00:00 AM), the system 100 may add each glucose exposure over the interval of sixty minutes over the course of the twenty-four hour day, so that, at a particular hour (e.g., 9:00 AM), the system 100 may determine the total glucose exposure for the user for the day at 9:00 AM.

In an alternate embodiment, the system 100 may utilize a weighted average for determining the glucose exposure over the interval of time. In this alternate embodiment, the system 100 may give more weight to the glucose data received closer to the end of the interval of time and less weight to the glucose data received nearer to the beginning of the interval of time, so that the glucose exposure over the interval of time is closer to the current glucose exposure at the end of the interval of time. For example, in this alternate embodiment, if the system 100 received, in order, the glucose data at the particular interval of 90, 92.5, 97.5, and 100 (in units of measurement such as, e.g., in milligrams) over the interval of time, the weighted average may be greater than the actual average 95 of the glucose data.

As described in step 808, in various embodiments, the system 100 may determine a target glucose exposure for a particular hour. In one or more embodiments, and as shown in more detail in FIG. 8B, the target glucose exposure for the particular hour may be the amount of glucose exposure the user is trying to attain for the particular hour. As discussed in more detail below, in some embodiments, step 808 includes dividing a 24 hour glucose exposure limit by 24 to get a glucose exposure limit per hour (step 812) and multiplying the glucose exposure limit per hour by a numerical expression of the particular hour (step 814). In some embodiments, the target glucose exposure for the particular hour may be a limit of glucose exposure that the user is trying not to exceed. In at least one embodiment, the particular hour may be a specific time during a twenty-four hour period. For example, in one embodiment, the particular hour may be 9:00 AM.

As described in step 810, in multiple embodiments, the monitoring device 175 may display the glucose exposure as a proportion of the target glucose exposure for the particular hour. In at least one embodiment, the system 100 may compare the running total of the glucose exposure for the user at the particular hour to the target glucose exposure for the particular hour. In an alternate embodiment, the system 100 may compare the glucose exposure over the interval of time to the glucose exposure limit per hour.

For example, in several embodiments, if the interval of time is sixty minutes, then the system 100 will determine the glucose exposure (or average glucose level) of the user every sixty minutes. Continuing with the example, in some embodiments, the running total of glucose exposure at a particular hour may be the sum of the determined glucose exposure data (or average glucose levels) from the previous intervals of time for the day. Still continuing with this example, in many embodiments, if the interval of time is sixty minutes, the running total of glucose exposure at 10:00 AM may be the sum of the determined glucose exposures from 1:00 AM, 2:00 AM, 3:00 AM . . . 10:00 AM. Still continuing with this example, in one or more embodiments, if the previous determined glucose exposures for the day were 63 (00:00 AM), 60, 65, 73, 80, 84, 88, 90, 93, 95, and 97 (10:00 AM), then the running total of the glucose exposure at 10:00 AM is 888 units of measurement of glucose exposure. Continuing with this example, in one embodiment, if the target glucose exposure for 10:00 AM is 910 units of measurement of targeted glucose exposure, the monitoring device 175 may display 888 units of measurement of glucose exposure divided by 910 units of measurement of targeted glucose exposure. In a further embodiment, the monitoring device 175 may display the proportion of the glucose exposure to the target glucose exposure as a percentage.

In various embodiments, the system 100 may determine a 24-hour average glucose for the user. In many embodiments, the system may calculate the 24-hour average glucose by averaging the user's determined glucose exposure data from the previous 24-hour period. In some embodiments, the 24-hour average glucose may be a rolling average such that the 24-hour average glucose may be recalculated once an hour or once every interval of time in which the glucose exposure is determined. For example, in one embodiment, the 24-hour average glucose at 11:00 AM may be an average of the determined glucose exposure data for the previous 24 hours (e.g., from about 11:00 AM previous day to 11:00 AM current day), while the glucose exposure at the particular hour (11:00 AM) may be the sum of the glucose exposure data from midnight of the current day to 11:00 AM of the current day (eleven hours). In at least one embodiment, the system may display the 24-hour average glucose. In one or more embodiments, the system may compare the current 24-hour period to an immediately preceding 24-hour average glucose. In one embodiment, the system 100 may display the difference between the current 24-hour average glucose to the immediately preceding 24-hour average glucose as a percentage. In some embodiments, system 100 may store the 24-hour average glucose determinations for previous days (e.g., the 24-hour average glucose determination from midnight (00:00 AM) to the next midnight (24:00) to be utilized in additional calculations.

In several embodiments, the system 100 may determine a seven-day average glucose for the user. In some embodiments, the system may calculate the seven-day average glucose by averaging the user's determined glucose exposure data from the previous seven-day period. In one or more embodiments, the system 100 may average the determined 24-hour average glucose for each of the preceding seven days to determine the seven-day average glucose. In at least one embodiment, the system 100 may display the seven-day average glucose. Similarly, in many embodiments, the system 100 may determine an average glucose for any time period (e.g., one month, one year), by averaging 24-hour average glucose determinations or seven-day average glucose determinations, or other similar glucose exposure calculations. In one embodiment, the system 100 may determine a median to calculate the 24-hour average glucose and/or seven-day average glucose.

Figure 8B:
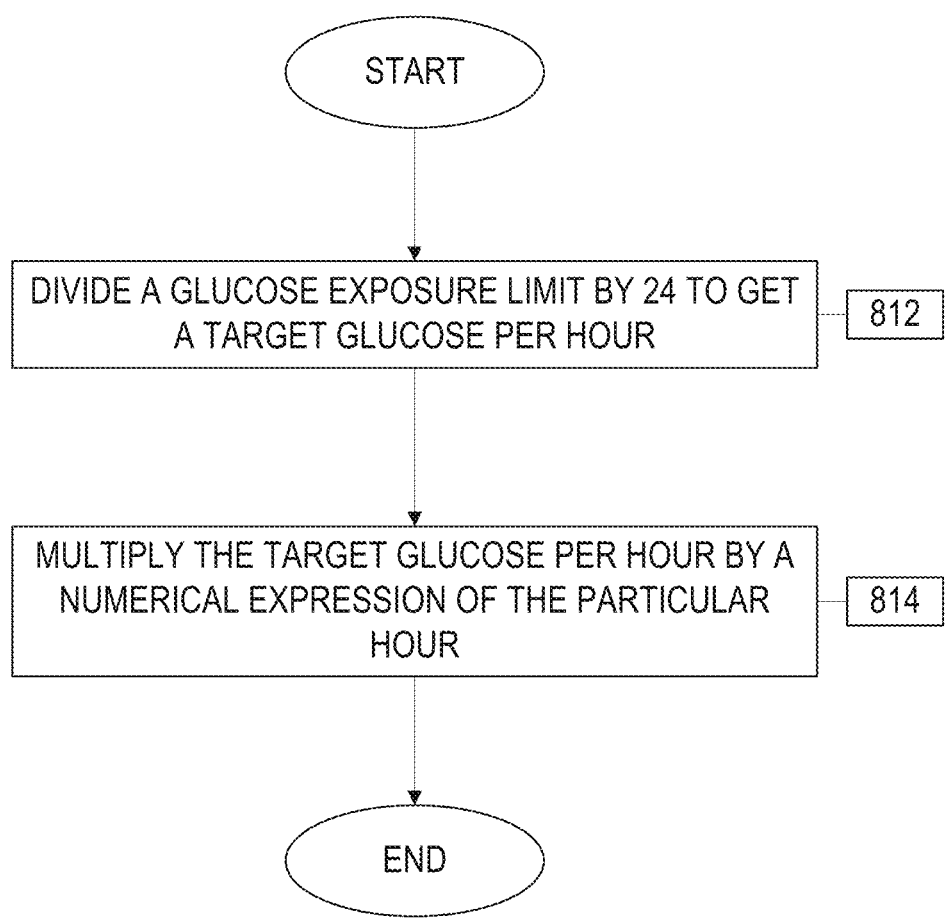
FIG. 8B is a flow chart of an exemplary target glucose exposure determination process, according to one embodiment of the present disclosure.

Turning now to FIG. 8B, an exemplary target glucose exposure determination process 808 is shown, according to one embodiment of the present disclosure. In multiple embodiments, as shown in step 812, in order to determine a target glucose exposure for a particular hour, the system 100 may first divide a glucose exposure limit by 24 to get a glucose exposure limit per hour. In one or more embodiments, the glucose exposure limit may be the maximum amount of glucose exposure the user desires over the course of a twenty-four hour day. In at least one embodiment, the user may input the glucose exposure limit into the user input 125. For example, in one embodiment, the user may input a glucose exposure limit of 1200 units of measurement of glucose exposure into the user input 125, which the system 100 divides by 24 to determine that the glucose exposure limit per hour is 50 units of measurement of glucose exposure.

In various embodiments, as shown in step 814, the system 100 may multiply the glucose exposure limit per hour by a numerical expression of the particular hour. In many embodiments, the numerical expression of the particular hour correlates to the particular time of day, using a 00:00-24:00 time measure for the time of day. For example, in one embodiment, the particular hour 11:00 AM correlates to 11 for the numerical expression of the particular hour. In a further embodiment, the minutes portion of the time of day correlates to a decimal for the numerical expression of the particular hour. For example, in the further embodiment, the time of day 5:15 PM correlates to 17.25 for the numerical expression of the particular hour.

As will be understood from discussions herein, the particular hour may be any hour within a 24 hour period (or other time period). In various embodiments, when a measurement is taken or a value is determined or calculated for a particular hour, it may the hour ending at a particular time. For example, in one embodiment, if the particular hour is 9:00 AM, then the system may calculate glucose exposure from 8:01 AM or 8:00 AM to 9:00 AM.

According to one embodiment, as an example of steps 812 and 814, in multiple embodiments, the user may input a glucose exposure limit of 1800 units of measurement. In many embodiments, the system 100 may then divide the glucose exposure limit by 24, to get a glucose exposure limit per hour of 75 units of measurement per hour. Next, in several embodiments, if the particular hour is 3:00 PM, the system 100 may multiple the glucose exposure limit per hour by the numerical expression of 3:00 PM, which is 15. In one or more embodiments, the system 100 may determine that the target glucose exposure for 3:00 PM is 75 units of measurement per hour multiplied by 15 hours, which is 1125 units of measurement of glucose exposure.

In an alternative embodiment, the system 100 may divide the glucose exposure limit by 1440 to get a target glucose per minute. Continuing with this alternative embodiment, the system 100 may multiply the target glucose per minute by a numerical expression of a particular minute. In this alternative embodiment, the particular minute may be a specific minute during the day such that the numerical expression of the particular minute is between 0 and 1440. For example, still continuing in the alternative embodiment, at 1:45 PM, the particular minute is equal to thirteen hours multiplied by 60, and then added to the remaining 45 minutes, which is 825 minutes. In various embodiments, the monitoring device 175 may display the glucose exposure as a proportion to the target glucose exposure for the particular minute. In a further embodiment, similar analysis may be done so that the system 100 may determine a target glucose exposure for a particular second.

In a further embodiment, the glucose exposure limit may be a function of the user's personal information, such as, but not limited to, the user's height, weight, body mass index score, average 24 hour exercise, average 24 hour glucose exposure, whether the user is preparing for an endurance contest, and/or other similar information. In this embodiment, the system 100 may calculate a healthy glucose exposure limit, based on algorithms and based on the user's personal health targets. For example, in one embodiment, the user may want to lose weight, so the user may input a "lose weight" target into the user input 125, and based on the user's personal information and other factors, the system 100 determines a glucose exposure limit for the user.

In a further embodiment, the communications interface 165 may import or receive data from other devices that determine data about a user (or about other users). In various embodiments, the system 100 may store data in a storage module 150 with other data for other users. In one or more embodiments, data may include the user's personal information, as well as the user's historical glucose data. In at least one embodiment, if a user updates the user's personal information and the update includes a change in body mass index score or weight, the system 100 may determine if the user has increased or decreased glucose exposure. In a further embodiment, the analysis module 140 may deploy machine learning or AI to optimize the glucose exposure limits for a variety of user body types, by using measured glucose data against increases and decreases in users' weight and body mass index scores.

In various embodiments, the system 101, at step 808, may receive, from the user or the system, a glucose exposure limit per hour. In several embodiments, the glucose exposure limit per hour may be utilized to calculate the target glucose exposure for a particular hour by multiplying the glucose exposure limit per hour by the numerical expression of the particular hour, as discussed infra. In one or more embodiments, the glucose exposure limit per hour may be multiplied by 24 to get a 24-hour glucose exposure limit. For example, in one embodiment, the user or the system may provide a glucose exposure limit per hour of 80 mg/dL, which the system may then multiply by 24 to determine the glucose exposure limit. Continuing with the example, in some embodiments, if the user checks his glucose exposure at 3:00 PM, and the 24-hour period began at midnight (00:00 AM), the system would multiply the glucose exposure limit per hour by 15 to get the target glucose exposure for the particular hour (1200 mg/dL). Still continuing with the above example, in many embodiments, the system may thereafter compare the user's glucose exposure with the target glucose exposure for the particular hour, and may also display the 24-hour glucose exposure limit.

Figure 9A:
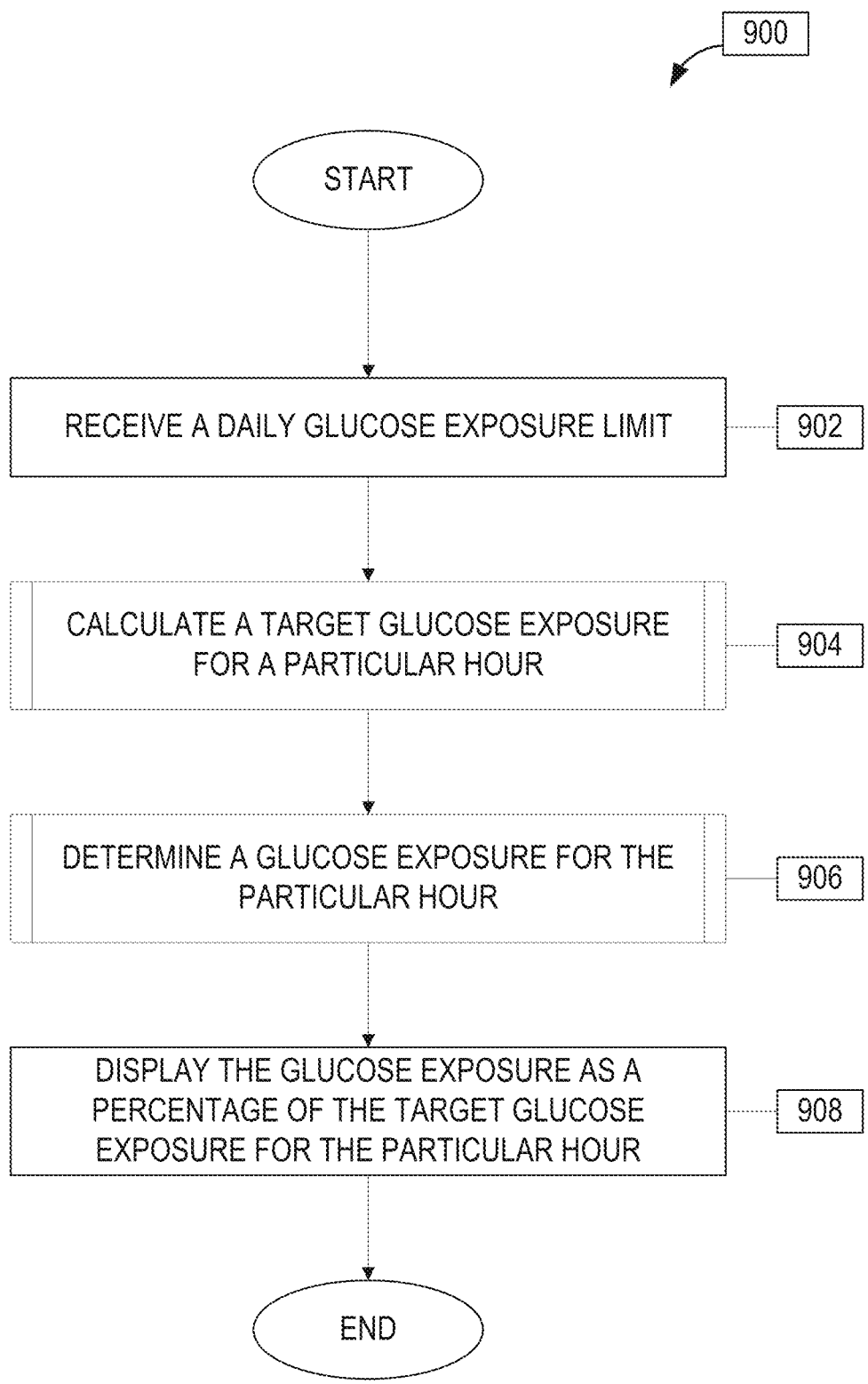
FIG. 9A is a flow chart of an exemplary glucose exposure process, according to one embodiment of the present disclosure.

An exemplary glucose exposure process 900 is shown in FIG. 9A, according to one embodiment of the present disclosure. In various embodiments, a user may first connect the continuous biomarker sensor 220 to the user's body, such that the continuous biomarker sensor 220 is interacting with the interstitial fluid or other bodily fluid.

As shown in step 902 of process 900, in multiple embodiments, the system 100 may receive a 24 hour glucose exposure limit. In one or more embodiments, the user may input the 24 hour glucose exposure limit into the system 100 via the user input 125. In at least one embodiment, the 24 hour glucose exposure limit may be the maximum amount of glucose exposure the user desires to receive over the course of a twenty-four hour day. In one or more embodiments, a medical practitioner (other suitable user) may input the 24 hour glucose exposure limit into the system 100 via the user input 125. In a further embodiment, a physician or other medical practitioner may prescribe a specific 24 hour glucose exposure limit for the user. In some embodiments, the system 100 may calculate the glucose exposure limit based on weight reduction targets, machine learning and artificial intelligence, physical activity targets, or other analysis.

At step 904, in various embodiments, the system 100 may calculate a target glucose exposure for a particular hour. As discussed in more detail below (in reference to FIG. 9B), in some embodiments, step 904 includes dividing a glucose exposure limit by 24 to get a glucose exposure limit per hour (step 910) and multiplying the glucose exposure limit per hour by a numerical expression of the particular hour (step 912). In one or more embodiments, the target glucose exposure for the particular hour may be the amount of glucose exposure the user is trying to attain for the particular hour. In many embodiments, the target glucose exposure for the particular hour may be a limit of glucose exposure that the user is trying not to exceed. In at least one embodiment, the particular hour may be a specific time during a twenty-four hour period. For example, in one embodiment, the particular hour may be 9:00 AM.

As shown in step 906, in several embodiments, the system 100 may determine a glucose exposure for the particular hour. As discussed in more detail below (in reference to FIG. 9C), in some embodiments, step 906 includes determining if a Bluetooth radio is connected to the continuous biomarker sensor 220 (step 914), and if so, receiving, via the Bluetooth radio from the continuous biomarker sensor 220, obfuscated glucose data (step 916), deobfuscating the data (step 918), and determining the glucose exposure over a time period based on the glucose data received at the predetermined interval (step 920), and if the Bluetooth radio is not connected to the sensor, determining an average glucose exposure for the particular hour based on historical data (step 922), and using the average glucose exposure for the particular hour as the glucose exposure for the particular hour (step 924).

At step 908, in many embodiments, the monitoring device 175 may display the glucose exposure calculated at step 906 as a percentage of the target glucose exposure for the particular hour calculated at step 904. For example, in one embodiment, the glucose exposure calculated at step 906 may be 1140 at the particular hour, and the target glucose exposure for the particular hour is 1080, which would be displayed as 105.5%.

Figure 9B:
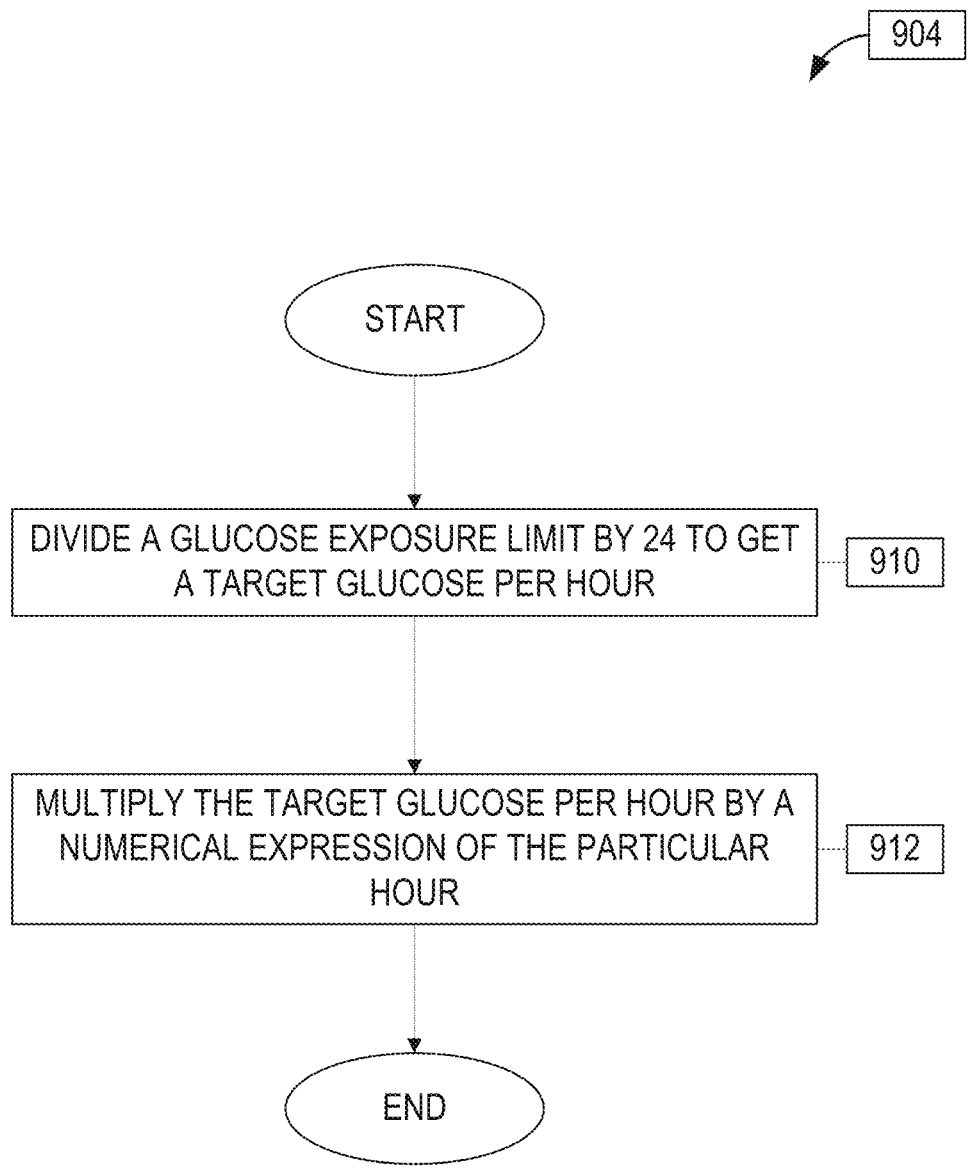
FIG. 9B is a flow chart of an exemplary target glucose exposure calculation process, according to one embodiment of the present disclosure.

As described in FIG. 9B, an exemplary target glucose exposure determination process 904 is shown, according to one embodiment of the present disclosure. As described in step 910, in multiple embodiments, in order to determine a target glucose exposure for a particular hour, the system 100 may first divide the 24 hour glucose exposure limit by 24 to get a glucose exposure limit per hour. For example, in one embodiment, the user may input a glucose exposure limit of 1200 units of measurement of glucose exposure into the system 100, which the system 100 divides by 24 to determine that the glucose exposure limit per hour is 50 units of measurement of glucose exposure.

In various embodiments, as shown in step 912, the system 100 may multiply the glucose exposure limit per hour by a numerical expression of the particular hour. In many embodiments, the numerical expression of the particular hour correlates to the particular time of day, using a 00:00-24:00 time measure for the time of day. For example, in one embodiment, the particular hour 11:00 AM correlates to 11 for the numerical expression of the particular hour. In a further embodiment, the minutes portion of the time of day correlates to a decimal for the numerical expression of the particular hour. For example, in the further embodiment, the time of day 5:15 PM correlates to 17.25 for the numerical expression of the particular hour.

According to one embodiment, as an example of steps 910 and 912, in multiple embodiments, the user may input a glucose exposure limit of 1800 units of measurement. In many embodiments, the system 100 may then divide the glucose exposure limit by 24, to get a glucose exposure limit per hour of 75 units of measurement per hour. Next, in several embodiments, if the particular hour is 3:00 PM, the system 100 may multiple the glucose exposure limit per hour by the numerical expression of 3:00 PM, which is 15. In one or more embodiments, the system 100 may determine that the target glucose exposure for 3:00 PM is 75 units of measurement per hour multiplied by 15 hours, which is 1125 units of measurement of glucose exposure.

Figure 9C:
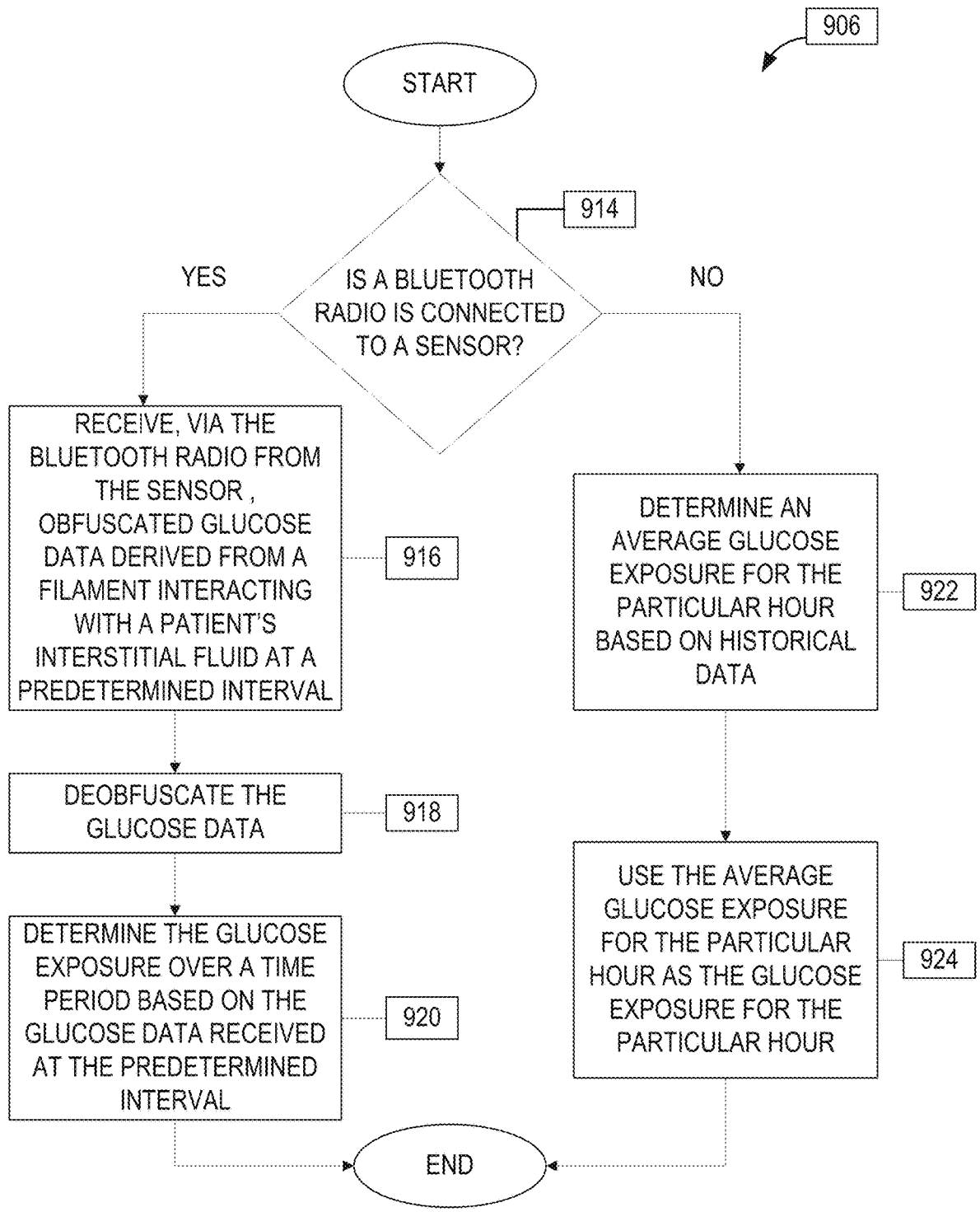
FIG. 9C is a flow chart of an exemplary glucose exposure for a particular hour determination process, according to one embodiment of the present disclosure.

FIG. 9C shows an exemplary glucose exposure for a particular hour determination process 906, according to one embodiment of the present disclosure. In various embodiments, at step 914 of process 906, the system 100 determines whether a Bluetooth radio is connected to the continuous biomarker sensor 220. In one or more embodiments, the system 100 is wirelessly connected to the continuous biomarker sensor 220 via the communications interface 165.

In multiple embodiments, as shown in step 916, if a Bluetooth radio is connected to the continuous biomarker sensor 220, then the system 100 receives, via the Bluetooth radio from the continuous biomarker sensor 220, obfuscated glucose data derived from the continuous biomarker sensor 220 interacting with a patient's interstitial fluid at a predetermined interval. In one or more embodiments, the predetermined interval may be the time between the system 100 receiving glucose data from the continuous biomarker sensor 220. In at least one embodiment, the predetermined interval may be one second, such that the system 100 is essentially constantly receiving obfuscated glucose data. In some embodiments, the predetermined interval may be one hour, such that the system 100 receives obfuscated glucose data once per hour. In many embodiments, the predetermined interval may be one day or multiple days.

In multiple embodiments, the continuous biomarker sensor 220 may collect glucose data over a predetermined interval, but, instead of transmitting each glucose data individually, the continuous biomarker sensor 220 may store the glucose data and batch the glucose data for transmitting. In many embodiments, the continuous biomarker sensor 220 may transmit a batch of glucose data to the monitoring device 175 via the communications interface 165 after a specific amount of time or after a specific amount of glucose data has been collected. For example, in this embodiment, the continuous biomarker sensor 220 may collect the glucose data at a constant rate (e.g., one per second), and only transmit the glucose data to the monitoring device 175 via the communications interface 165 once the continuous biomarker sensor 220 has collected a specific amount of glucose data (e.g., every five, ten, or twenty glucose data) (e.g., in a batch). In one embodiment, the predetermined interval may be the amount of time between the continuous biomarker sensor 220 conducting readings of glucose data.

As described in step 918, in various embodiments, the system 100 deobfuscates the glucose data. In one or more embodiments, the monitoring device 175, the integration module 130, or the analysis module 140 may deobfuscate the glucose data. In some embodiments, the monitoring device 175 may receive the obfuscated glucose data via the communications interface 165 (e.g., Bluetooth radio). In at least one embodiment, the monitoring device 175, after receiving the obfuscated glucose data, may deobfuscate the glucose data or send the obfuscated glucose data to the integration module 130 or the analysis module 140, to deobfuscate the glucose data. In one embodiment, if the monitoring device 175 sends the obfuscated glucose data to the integration module 130 or the analysis module 140, the integration module 130 or the analysis module 140 may deobfuscate the glucose data and thereafter transmit the deobfuscated glucose data to the monitoring device 175. In many embodiments, once the glucose data is deobfuscated, the system 100 may read and utilize the glucose data.

As shown in step 920, in several embodiments, the system 100 determines the glucose exposure over a time period based on the glucose data received at the predetermined interval. In at least one embodiment, the glucose exposure over a time period may be an average of the glucose data received at the predetermined interval over the course of the time period.

In many embodiments, the time period (or time interval) may be an overall amount of time from which the glucose exposure is being measured. For example, in one embodiment, the system 100 may determine the glucose exposure at the time 8:00 AM (the particular hour). Continuing with the example, in some embodiments, the time period may be from 00:00 AM to 8:00 AM, such that the system 100 determines the glucose exposure for the time period.

In another example, in at least one embodiment, the system 100 may determine the glucose exposure at the time 8:00 AM (the particular hour) and the time period may be one hour. Continuing with this example, the system 100 may determine the glucose exposure for each time period, and determine the glucose exposure at 8:00 AM by summing up the individual glucose exposures for each hour (or other increment of time) throughout the day. In one or more embodiments, the time period may range from one second to one day (such as, e.g., 15 minutes, 30 minutes, 1 hour, 3 hours, 1 day, etc.).

For example, in one embodiment, the predetermined interval may be one minute, and the time period may be thirty minutes, such that the system 100 receives glucose data from the continuous biomarker sensor 220 thirty times within the time period. Continuing with the example, in at least one embodiment, the system 100 may calculate the average of the thirty glucose data points to determine the glucose exposure over the period of time. In an alternate embodiment, the system 100 may calculate a weighted average of the thirty glucose data points, such that the later received glucose data points have more weight than the earlier received glucose data points.

In a further embodiment, the system 100 may calculate a running total of glucose exposure through a twenty-four hour day by adding the determined glucose exposures over the time periods throughout the twenty-four hours. For example, in one embodiment, if the time period is sixty minutes, and the twenty-four hour day begins at midnight (00:00 AM), the system 100 may add each glucose exposure (in units of measurement) for each sixty minute time period over the course of the twenty-four hour day, so that, at a particular hour (e.g., 9:00 AM), the system 100 may determine the total glucose exposure for the user for the day at 9:00 AM.

In one or more embodiments, the system 100 may be configured to compensate for a disconnected sensor and may use one or more smoothing algorithms (or the like) to fill in or approximate glucose exposure for an hour (or other suitable time period). For example, if a user is sleeping and is not wearing a sensor, the system may use historical or other data to estimate the user's glucose exposure while the sensor is disconnected.

At step 922, in multiple embodiments, if a Bluetooth radio, for example, is not connected to the continuous biomarker sensor 220, the system 100 determines an average glucose exposure for the particular hour based on historical data. In this embodiment, since the system 100 is not connected to the continuous biomarker sensor 220, the system 100 may not be able to receive current glucose data at the predetermined interval from the continuous biomarker sensor 220. In many embodiments, the system 100 may store historical glucose data in the storage module 150 such that the system 100 may retrieve historical glucose data from previous days and utilize the historical data in the present average glucose exposure determination. In one or more embodiments, the utilization of the historical data allows the system 100 to continue to calculate the total glucose exposure and display the glucose exposure as a percentage of the target glucose exposure for the particular hour. In at least one embodiment, the historical data may include particular hour information, such that the system 100 may incorporate historical data from the same particular hour as the particular hour glucose data that is missing due to the system 100 not being connected to the continuous biomarker sensor 220.

For example, in one embodiment, the Bluetooth radio may not be connected to the continuous biomarker sensor 220 from 2:00 PM (or 2:01 PM) to 3:00 PM. Continuing with the example, in several embodiments, the system 100 may retrieve stored historical data from previous days that have a timestamp between 2:00 and 3:00 PM, and average the stored historical data for the particular hour to get an average glucose exposure for the particular hour based on historical data. In an alternative embodiment, the system 100 may determine a weighted average for the glucose exposure for the particular hour based on historical data, such that the more recent historical data is given more weight than the older historical data, because the more recent historical data is more likely to be more accurate to the actual current glucose exposure.

In at least one embodiment, if the system 100 does not receive the glucose data from the continuous biomarker sensor 220 at the particular interval, the system 100 may apply one or more smoothing algorithms once the system 100 is reconnected to the continuous biomarker sensor 220, to back fill the missing glucose data. In one or more embodiments, the one or more smoothing algorithms may include calculating an average glucose exposure based on the glucose data received before and after the system 100 stopped receiving glucose data from the continuous biomarker sensor 220. For example, in one embodiment, if the system 100 did not receive glucose data for one predetermined interval, the system 100 may utilize immediately preceding glucose data for at least one predetermined interval and immediately succeeding glucose data for at least one predetermined interval, and average the at least two glucose data points together to determine the missing glucose data for the predetermined interval. In at least one embodiment, the system 100 may utilize multiple immediately preceding glucose data points and multiple immediately succeeding glucose data points to determine the missing glucose data for the predetermined interval. In many embodiments, the user's glucose exposure does not vary much from one predetermined interval to the next, so the system 100 is able to take an average from the glucose data from preceding and succeeding glucose data to fill in a missing glucose data point with a high level of accuracy.

In one or more embodiments, the system 100 may utilize a combination of historical data and an average of recent data to determine missing glucose data points. For example, in one embodiment, if the system 100 is missing a glucose data point for 10:00 AM, the system 100 may retrieve historical glucose exposure data for 10:00 AM for the user, as well as calculate an average of recent preceding and succeeding glucose data, and determine or estimate the missing glucose data point from a combination of the historical glucose exposure data and the average of recent preceding and succeeding glucose data. In a further embodiment, the system 100 may also utilize other users' glucose exposure data to determine missing glucose data points. In this further embodiment, the system 100 may recognize other users as similar to the user with missing glucose exposure data, based on similarities in the users' profiles, such as the users' age, gender, height, weight, similarity in glucose exposure, and other similar factors.

In various embodiments, the system 100 may notify the user if the system 100 determines that the user's glucose exposure is higher or lower than the target glucose exposure for a particular hour by a more than a certain percentage. For example, in at least one embodiment, system 100, via the monitoring device 175, may notify the user if the user's glucose exposure is ten percent (or more) greater than or less than the user's target glucose exposure for a particular hour. In many embodiments, the system 100 may notify the user via displaying a message on the monitoring device 175 or causing a push notification, SMS message, email, or other similar communication to display on or transmit to a secondary device.

In one or more embodiments, if the user's glucose exposure is greater than the user's glucose target for a particular hour, the system 100 may make suggestions to the user so that the user's glucose exposure may decrease in forthcoming hour(s). In some embodiments, the suggestions may include, but are not limited to, eating low-carbohydrate foods, exercising, including a specific intensity level of exercising (such as, e.g., walking, jogging, running), taking insulin (for diabetic users), including rapid-acting insulin, short-acting insulin, intermediate-acting insulin, mixed-insulin, and long-acting insulin, or a combination of suggestions. In at least one embodiment, the active component 185 may administer the insulin to the user. In one embodiment, if the user has indicated to the system that the user's is preparing for future physical activity (such as, e.g., running a marathon), the system 100 may not notify the user if the user's glucose exposure exceeds the glucose target for a particular hour.

In multiple embodiments, the if the user's glucose exposure is less than the user's target glucose exposure for a particular hour by a certain amount, the system 100 may recommend the user take an action to increase the user's glucose exposure. In some embodiments, situations in which the system 100 may notify the user to increase the user's glucose exposure may include, but is not limited to, the user ingesting carbohydrates in preparation for a physical activity (such as, e.g., a triathlon), hypoglycemia, or other situations in which the user's glucose exposure is lower than the target glucose exposure for a particular hour. In many embodiments, the system 100 may recommend to a user via the monitoring device 175 to consume carbohydrates to increase the user's glucose exposure if the user's glucose exposure is less than the target glucose exposure for a particular hour. For example, in one embodiment, a user may indicate to the system 100 that the user is attempting to reach or surpass the target glucose exposure for a particular hour in preparation to run a marathon, and so if the user's glucose exposure is five percent lower than the target glucose exposure for a particular hour, the system 100 may notify the user, via the monitoring device 175, and recommend the user ingest carbohydrates. In at least one embodiment, the system 100 may recommend the user seek medical treatment, such as but not limited to, going to an emergency room or calling an ambulance, or other similar medical treatment, if the user's glucose exposure is low enough to be considered hypoglycemic.

Figure 10:
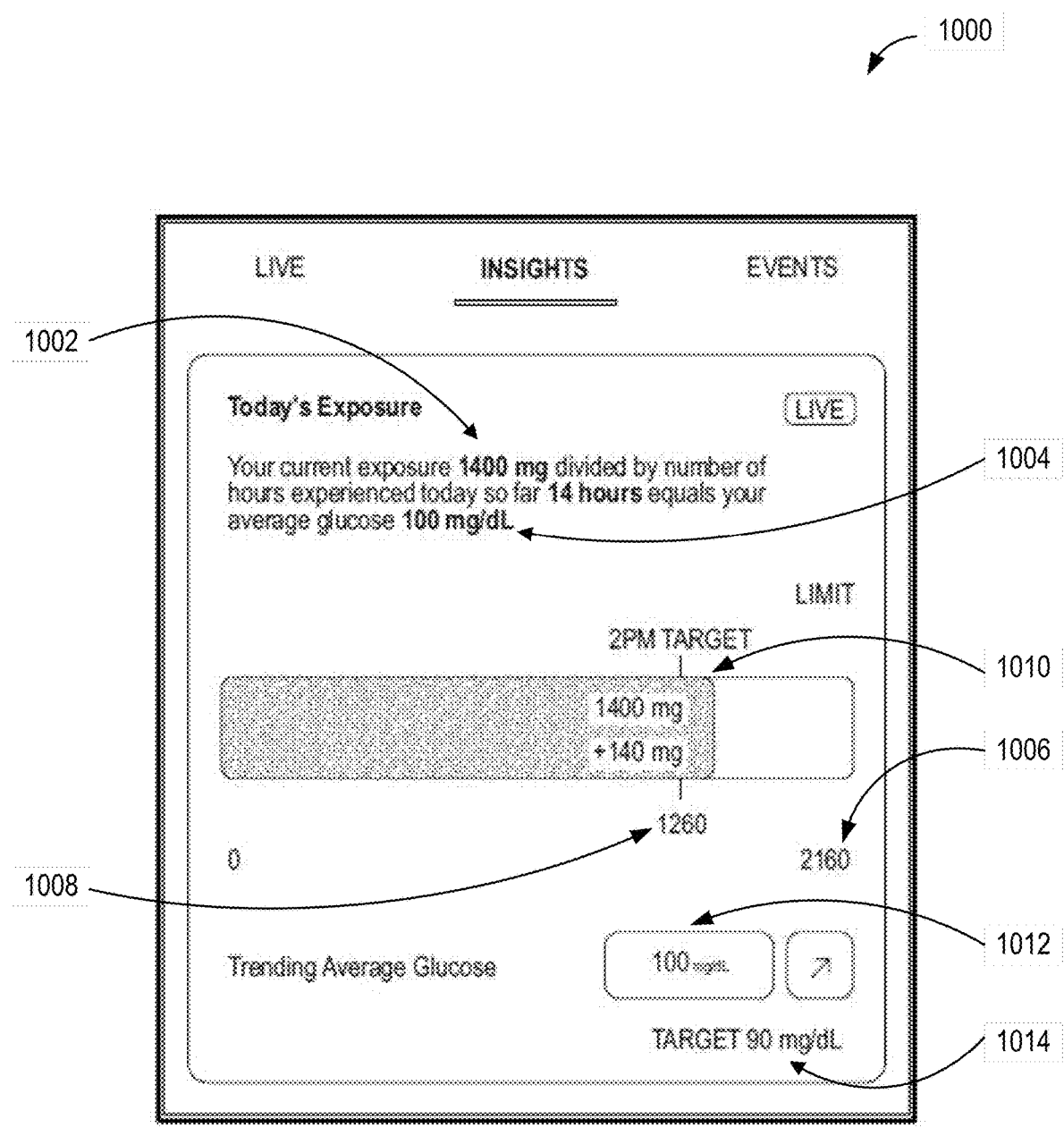
FIG. 10 is an exemplary user interface, according to one embodiment of the present disclosure.

Turning now to FIG. 10, an exemplary user interface 1000 for the glucose exposure process is shown, according to one embodiment of the present disclosure. In various embodiments, user interface 1000 may represent a monitoring device 175. In one or more embodiments, the user interface 1000 may display a user's current glucose exposure (as shown by 1002), a user's average glucose per hour (as shown by 1004), a user's glucose exposure limit for a 24 hour period (as shown by 1006), a user's target glucose for a particular hour (as shown by 1008), a comparison of the user's current glucose exposure to the target glucose for a particular hour (as shown by 1010), and/or a user's trending average glucose (as shown by 1012) and a target average glucose for the user over a 24 hour period (as shown by 1014).

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable non-volatile memories such as secure digital (SD), flash memory, memory stick, etc., or any other medium which can be used to carry or store computer program code in the form of computer-executable instructions or data structures and which can be accessed by a computer.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a computer to perform one specific function or a group of functions.

Those skilled in the art will understand the features and aspects of a suitable computing environment in which aspects of the disclosure may be implemented. Although not required, some of the embodiments of the claimed systems and processes may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the processes disclosed herein. The particular sequence of such executable instructions or associated data structures represent examples for implementing the functions described in such steps.

Those skilled in the art will also appreciate that the claimed and/or described systems and processes may be practiced in network computing environments with many types of computer system configurations, including personal computers, smartphones, tablets, hand-held devices, multi-processor systems, microprocessor-based or programmable electronics, networked PCs, minicomputers, mainframe computers, and the like. Embodiments of the claimed systems and processes are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that effects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the systems and processes are embodied. The logical connections between computers include a local area network (LAN), a wide area network (WAN), virtual networks (WAN or LAN), and wireless LANs (WLAN) that are presented here by way of example and not limitation. Such networking environments are commonplace in enterprise-wide computer networks, intranets, and the Internet.

When used in a LAN or WLAN networking environment, a computer system implementing aspects of the systems and processes is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and process of the claimed systems and processes will be readily discernible from the description herein, by those of ordinary skill in the art. Many embodiments and adaptations of the disclosure and claimed systems and processes other than those herein described, as well as many variations, modifications, and equivalent arrangements and process, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed systems and processes. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed systems and processes. In addition, some steps may be carried out simultaneously, contemporaneously, or in synchronization with other steps.

The embodiments were chosen and described in order to explain the principles of the claimed systems and processes and their practical application so as to enable others skilled in the art to utilize the systems and processes and various embodiments and with various modifications as are suited to the particular use contemplated. Alternative embodiments will become apparent to those skilled in the art to which the claimed systems and processes pertain without departing from their spirit and scope. Accordingly, the scope of the claimed systems and processes is defined by the appended claims rather than the foregoing description and the exemplary embodiments described therein.

We claim:

1. A computer-implemented method in which one or more processing devices perform operations comprising:
   determining a glucose exposure for a particular hour based on glucose data received from a sensor on a particular interval;
   determining a target glucose exposure for the particular hour by multiplying a glucose exposure limit per hour by a numerical representation of the particular hour;
   receiving additional biomarker data comprising one or more of cardiovascular, pulmonary, and perspiratory data;
   integrating the glucose exposure for the particular hour and the additional biomarker data for display; and
   displaying the glucose exposure for the particular hour as a proportion of the target glucose exposure for the particular hour and the additional biomarker data on a display.

2. The computer-implemented method of claim 1, wherein the glucose data comprises a glucose reading taken from a filament interacting with interstitial fluid.

3. The computer-implemented method of claim 1, the operations further comprising determining an average glucose level for the particular hour by averaging one or more glucose readings received on the particular interval during the particular hour.

4. The computer-implemented method of claim 3, wherein the particular interval is 15 minutes.

5. The computer-implemented method of claim 3, wherein the particular interval is 1 minute.

6. The computer-implemented method of claim 3, wherein the operation of determining the glucose exposure for the particular hour comprises adding the average glucose level for the particular hour to a summation of average glucose levels of the patient for hours preceding the particular hour in a 24-hour period.

7. The computer-implemented method of claim 6, wherein the 24-hour period begins at midnight.

8. The computer-implemented method of claim 7, wherein:
   the particular interval is 15 minutes;
   the particular hour is 9:00 AM and defined by 60 minutes between 8:01 AM to 9:00 AM;

determining the average glucose level for 8:01 AM to 9:00 AM by averaging one or more glucose readings received every 15 minutes during the particular hour;

determining the glucose exposure for 8:01 AM to 9:00 AM comprises adding the average glucose level for 8:01 AM to 9:00 AM to a summation of average glucose levels of the patient from midnight until 8:00 AM; and determining the target glucose exposure for 8:01 AM to 9:00 AM comprises multiplying the glucose exposure limit per hour by 9.

9. The computer-implemented method of claim 1, the operations further comprising:

detecting movement of a patient associated with the glucose exposure; and providing recommendations for meeting the glucose exposure limit based on the glucose exposure for the particular hour and the information associated with the movement of the patient.

10. A system comprising:

a processor; and a non-transitory computer-readable medium having instructions stored thereon, the instructions executable by the processor for performing operations comprising:

determining a glucose exposure for a particular hour based on glucose data received on a particular interval;

determining a target glucose exposure for the particular hour by multiplying a glucose exposure limit per hour by a numerical representation of the particular hour;

integrating the glucose exposure for the particular hour and additional biomarker data via the integration module for display; and displaying the glucose exposure for the particular hour as a proportion of the target glucose exposure for the particular hour and the additional biomarker data on a display.

11. The system of claim 10, wherein the operations further comprise deobfuscating obfuscated glucose data received from a sensor on the particular interval to generate the glucose data.

12. The system of claim 11, wherein the operation of deobfuscating the obfuscated glucose data comprises decrypting the obfuscated glucose data.

13. The system of claim 12, wherein the obfuscated glucose data comprises a glucose reading taken from a filament interacting with interstitial fluid.

14. The system of claim 10, wherein the operations further comprise receiving, from a sensor of a wearable computing device, the additional biomarker data comprising one or more of cardiovascular, pulmonary, and perspiratory data.

15. The system of claim 10, wherein the operations further comprise determining an average glucose level for the particular hour by averaging one or more glucose readings received on the particular interval during the particular hour.

16. A non-transitory computer-readable medium having program code that is stored thereon, the program code executable by one or more processing devices for performing operations comprising:

determining a glucose exposure for a particular hour based on glucose data received from a sensor on a particular interval;

determining a target glucose exposure for the particular hour by multiplying a glucose exposure limit per hour by a numerical representation of the particular hour;

integrating the glucose exposure for the particular hour and the additional biomarker data for display; and displaying the glucose exposure for the particular hour as a proportion of the target glucose exposure for the particular hour and the additional biomarker data on a display.

17. The non-transitory computer-readable medium of claim 16, wherein the operations further comprise receiving, from a sensor of a wearable computing device, the additional biomarker data comprising one or more of cardiovascular, pulmonary, and perspiratory data.

18. The non-transitory computer-readable medium of claim 16, wherein the glucose data comprises a glucose reading taken from a filament interacting with interstitial fluid.

19. The non-transitory computer-readable medium of claim 16, the operations further comprising determining an average glucose level for the particular hour by averaging one or more glucose readings received on the particular interval during the particular hour.

20. The non-transitory computer-readable medium of claim 19, wherein the operation of determining the glucose exposure for the particular hour comprises adding the average glucose level for the particular hour to a summation of average glucose levels of the patient for hours preceding the particular hour in a 24-hour period.

* * * * *